United States Patent
Schugt et al.

(10) Patent No.: US 11,666,751 B2
(45) Date of Patent: Jun. 6, 2023

(54) COMBINATION OBSTRUCTIVE SLEEP APNEA TRIALING LEAD AND CHRONIC LEAD

(71) Applicant: Medtronic Xomed, Inc., Jacksonville, FL (US)

(72) Inventors: Michael A. Schugt, St. Paul, MN (US); Linnea R. Lentz, Stacy, MN (US)

(73) Assignee: Medtronic Xomed, Inc., Jacksonville, FL (US)

( * ) Notice: Subject to any disclaimer, the term of this patent is extended or adjusted under 35 U.S.C. 154(b) by 58 days.

(21) Appl. No.: 16/752,087

(22) Filed: Jan. 24, 2020

(65) Prior Publication Data

US 2021/0228865 A1    Jul. 29, 2021

(51) Int. Cl.
*A61N 1/05*    (2006.01)
*A61N 1/375*   (2006.01)

(52) U.S. Cl.
CPC ....... *A61N 1/0548* (2013.01); *A61N 1/37518* (2017.08)

(58) Field of Classification Search
CPC .......................... A61N 1/0548; A61N 1/37518
See application file for complete search history.

(56) References Cited

U.S. PATENT DOCUMENTS

| | | |
|---|---|---|
| 5,146,918 A | 9/1992 | Kallok et al. |
| 5,540,733 A | 7/1996 | Testerman et al. |
| 5,546,952 A | 8/1996 | Erickson |
| 5,549,655 A | 8/1996 | Erikcson |
| 5,591,216 A | 1/1997 | Testerman et al. |
| 5,662,696 A * | 9/1997 | Kroll .................... A61N 1/3943 607/116 |
| 6,044,297 A | 3/2000 | Sheldon et al. |
| 6,269,269 B1 | 7/2001 | Ottenhoff et al. |
| 6,345,202 B2 | 2/2002 | Richmond et al. |
| 7,359,751 B1 * | 4/2008 | Erickson ............ A61N 1/37241 607/30 |

(Continued)

FOREIGN PATENT DOCUMENTS

WO    2017087681 A1    5/2017

OTHER PUBLICATIONS

Gharb et al., "Microsurgical Anatomy of the Terminal Hypoglossal Nerve Relevant for Neurostimulation in Obstructive Sleep Apnea," Neuromodulation: Technology at the Neural Interface, Aug. 5, 2015, 8 pp.

(Continued)

*Primary Examiner* — Catherine M Voorhees
*Assistant Examiner* — Roland Dinga
(74) *Attorney, Agent, or Firm* — Shumaker & Sieffert, P.A.

(57) ABSTRACT

In an example, the disclosure describes a system with a lead having a proximal end and a distal end and an elongated lead body. The lead has one or more electrodes. A fixation member is located on the elongated lead body and is configured to secure the lead to tissue within a patient. The fixation member is located on the lead so the fixation member is closer to the proximal end than the one or more electrodes of the lead. A trialing adaptor receives the proximal end of the lead and is removable when a trialing period is completed. A sheath encloses at least a portion of the lead and covers the fixation member. The sheath is configured to remain in place over the lead during the trialing period.

7 Claims, 10 Drawing Sheets

(56) References Cited

U.S. PATENT DOCUMENTS

| | | |
|---|---|---|
| 7,845,357 B2 | 12/2010 | Buscemi et al. |
| 8,366,615 B2 | 2/2013 | Razavi |
| 8,588,941 B2 | 11/2013 | Mashiach |
| 8,744,589 B2 | 6/2014 | Bolea et al. |
| 8,751,005 B2 | 6/2014 | Meadows et al. |
| 8,813,753 B2 | 8/2014 | Bhat et al. |
| 8,909,341 B2 | 12/2014 | Gelfand et al. |
| 9,486,628 B2 | 11/2016 | Christopherson et al. |
| 9,643,004 B2 | 5/2017 | Gerber |
| 9,662,045 B2 | 5/2017 | Skelton et al. |
| 9,662,497 B2 | 5/2017 | Meadows et al. |
| 9,849,289 B2 | 12/2017 | Mashiach et al. |
| 9,884,191 B2 | 2/2018 | Meadows et al. |
| 9,888,864 B2 | 2/2018 | Rondoni et al. |
| 9,889,299 B2 | 2/2018 | Ni et al. |
| 9,895,541 B2 | 2/2018 | Meadows et al. |
| 10,195,428 B2 | 2/2019 | Scheiner |
| 2002/0049479 A1 | 4/2002 | Pitts |
| 2003/0216789 A1 | 11/2003 | Deem et al. |
| 2004/0116977 A1* | 6/2004 | Finch ............... A61N 1/36021 607/46 |
| 2007/0123950 A1 | 5/2007 | Ludlow et al. |
| 2007/0173893 A1 | 7/2007 | Pitts |
| 2008/0103407 A1 | 5/2008 | Bolea et al. |
| 2008/0103576 A1 | 5/2008 | Gerber |
| 2008/0132970 A1* | 6/2008 | Barolat ............ A61N 1/36071 607/152 |
| 2008/0161874 A1 | 7/2008 | Bennett et al. |
| 2009/0259280 A1* | 10/2009 | Wilkin ............... A61N 1/057 607/116 |
| 2009/0270962 A1 | 10/2009 | Yang et al. |
| 2011/0270339 A1 | 11/2011 | Murray, III et al. |
| 2011/0270340 A1 | 11/2011 | Pellegrini et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2014/0031891 A1 | 1/2014 | Mashiach |
| 2014/0128951 A1* | 5/2014 | Kuntaegowdanahalli ............... A61N 1/05 607/116 |
| 2014/0135868 A1 | 5/2014 | Bashyam |
| 2014/0228905 A1 | 8/2014 | Bolea |
| 2014/0323839 A1 | 10/2014 | McCreery |
| 2015/0032177 A1* | 1/2015 | Mashiach ............... H02J 50/12 607/42 |
| 2015/0094790 A1* | 4/2015 | Shishilla ............ A61N 1/36017 607/116 |
| 2015/0100106 A1 | 4/2015 | Shishilla et al. |
| 2015/0105840 A1* | 4/2015 | Boggs, II ............ A61N 1/36071 607/46 |
| 2015/0142075 A1 | 5/2015 | Miller et al. |
| 2017/0080217 A1* | 3/2017 | Siegel ............... A61N 1/36132 |
| 2017/0151432 A1 | 6/2017 | Christopherson et al. |
| 2018/0117316 A1 | 5/2018 | Wagner et al. |
| 2019/0083793 A1* | 3/2019 | Nageri ............... A61N 1/0553 |
| 2019/0255339 A1* | 8/2019 | Lee ................... A61N 1/37205 |

OTHER PUBLICATIONS

Mu et al., "Human Tongue Neuroanatomy: Nerve Supply and Motor Endplates," Oct. 2010, accessed from NIH Public Access, 27 pp.

Heiser et al., "Surgical anatomy of the hypoglossal nerve: A new classification system for selective upper airway stimulation," Wiley Online, May 22, 2017, 10 pp.

Medtronic, "Basic Evaluation Procedure Technique Without Fluoroscopy—Part 3: Needle Placement," Training Video accessed from https://www.medtronic.com/us-en/healthcare-professionals/therapies-procedures/urology/sacral-neuromodulation/education-training/videos.html, webpage last updated Feb. 2018, 8 pp.

Medtronic, "Basic Evaluation Procedure Technique Without Fluoroscopy—Part 4: Test Lead Placement," Training Video accessed from https://www.medtronic.com/us-en/healthcare-professionals/therapies-procedures/urology/sacral-neuromodulation/education-training/videos.html, webpage last updated Feb. 2018, 8 pp.

Medtronic, "Basic Evaluation Procedure Technique Without Fluoroscopy—Part 5: Securing & Connecting Test Leads," Training Video accessed from https://www.medtronic.com/us-en/healthcare-professionals/therapies-procedures/urology/sacral-neuromodulation/education-training/videos.html, webpage last updated Feb. 2018, 8 pp.

U.S. Appl. No. 62/814,398, naming inventor Avram Scheiner, filed Mar. 6, 2019.

International Search Report and Written Opinion of International Application No. PCT/US2021/014164, dated May 10, 2021, 11 pp.

International Preliminary Report on Patentability from International Application No. PCT/US2021/014164 dated Aug. 4, 2022, 9 pp.

* cited by examiner

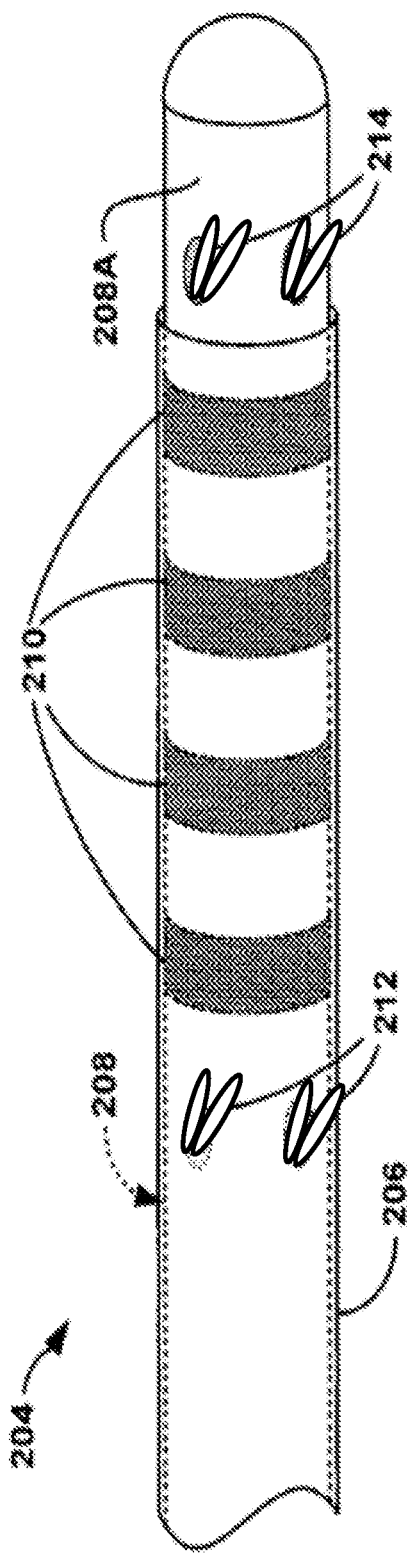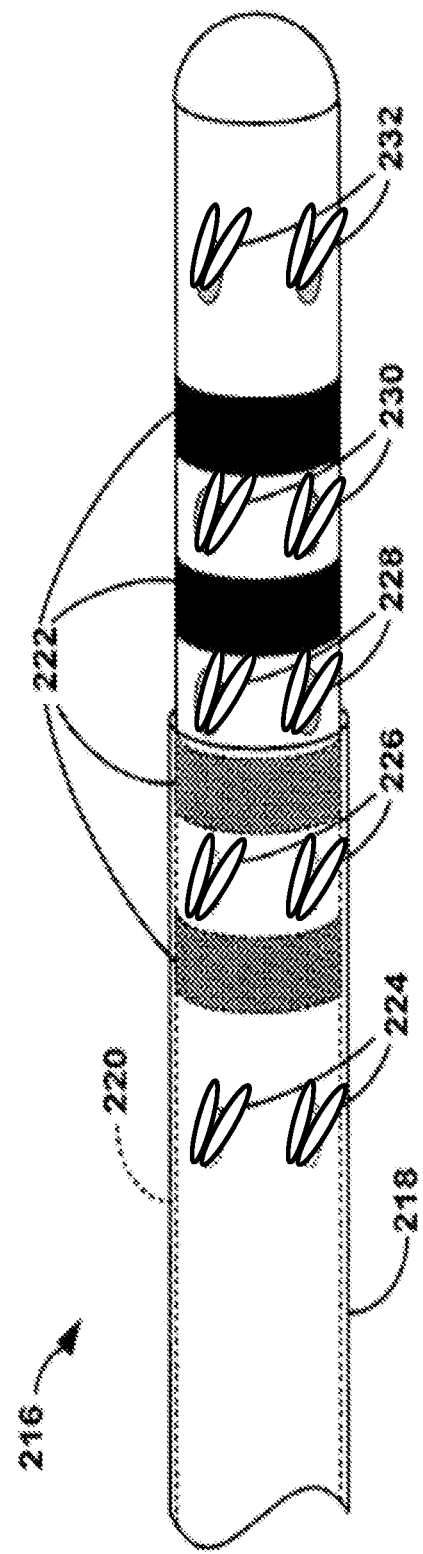
FIG. 9A
FIG. 9B

COMBINATION OBSTRUCTIVE SLEEP APNEA TRIALING LEAD AND CHRONIC LEAD

TECHNICAL FIELD

This disclosure relates to medical device systems and, more particularly, to medical device systems for delivery of electrical stimulation therapy.

BACKGROUND

Obstructive sleep apnea (OSA), which encompasses apnea and hypopnea, is a disorder in which breathing may be irregularly and repeatedly stopped and started during sleep, resulting in disrupted sleep and reduced blood oxygen levels. Muscles in a patient's throat intermittently relax thereby allowing soft tissues of the throat to obstruct the upper airway while sleeping and cause OSA. In patients with a smaller than normal airway, airflow into the upper airway may be obstructed by the tongue or soft pallet moving to the back of the throat and covering the airway. Loss of air flow also causes unusual inter-thoracic pressure as a person tries to breathe with a blocked airway. Lack of adequate levels of oxygen during sleep may contribute to abnormal heart rhythms, heart attack, heart failure, high blood pressure, stroke, memory problems, and increased accidents during the day due to inadequate sleep. Additionally, loss of sleep occurs when a person is awakened during an apneic episode.

SUMMARY

The devices, systems, and techniques of this disclosure generally relate to an implantable medical device (IMD) system and methods for therapy for obstructive sleep apnea (OSA) but may be extended to address other patient symptoms and disorders. With OSA, a patient's tongue may relax during sleep and block the patient's airway. Some example techniques to address OSA include electrically stimulating one or both hypoglossal nerves in the tongue of the patient. In response to the electrical stimulation, the hypoglossal nerve(s) causes protrusor muscles (e.g., genioglossus and geniohyoid muscles) to contract and move the tongue forward, thereby opening the airway. In some examples, in response to stimulating at the motor points of the protrusor muscles (e.g., a location where an axon of the hypoglossal nerve terminates at a muscle fiber), the protrusor muscles may contract to move the tongue forward, thereby opening the airway.

To stimulate the hypoglossal nerve(s) and/or motor points, a medical device outputs electrical stimulation therapy via one or more electrodes on one or more implanted leads to cause the tongue to move forward. A medical professional may implant the one or more leads into the tongue of the patient. The one or more implanted leads each include one or more electrodes coupled to the medical device (e.g., an implantable or external medical device delivering electrical stimulation via one or more electrodes on the lead).

With lead placement in the tongue, there may be issues related to how and where to place a lead to provide effective therapy. This disclosure describes example techniques for lead structures and/or lead placement that may overcome one or more issues. Although the example techniques are described with respect to lead placement in the tongue for treating OSA, the example techniques should not be considered to be limited to lead placement in the tongue or limited to treating OSA.

In an example, the disclosure describes a system with a lead having a proximal end and a distal end and an elongated lead body. The lead has one or more electrodes. A fixation member is located on the elongated lead body and is configured to secure the lead to tissue within a patient. The fixation member is located on the lead so the fixation member is closer to the proximal end than the one or more electrodes of the lead. A trialing adaptor receives the proximal end of the lead and is removable when a trialing period is completed. A sheath encloses at least a portion of the lead and covers the fixation member. The sheath is configured to remain in place over the lead during the trialing period.

In an example, the disclosure describes a system with an implantable medical lead configured to couple to a medical device to deliver a therapy from the medical device to a target therapy delivery site in a patient. The lead may have one or more electrodes and a fixation member disposed on the lead and configured to secure the lead to tissue of the patient at a plurality of points distributed around the lead. The fixation member is at a location distal to the medical device to deliver therapy. A sheath is able to receive the lead and cover the fixation member. The sheath is configured to remain in place over the at least a portion of the lead during a trialing period.

In an example, the disclosure describes a system with a medical lead with an elongated lead body having a proximal end and a distal end. There may be one or more electrodes disposed on the lead body distal end. A fixation member may be on the elongated lead body of the lead and able to secure the lead to tissue within a patient. The fixation member can be disposed proximal to the one or more electrodes. A sheath may cover the fixation member for a duration of a trialing period. The sheath can be removed from the lead to activate the fixation member and secure the medical lead to a tissue within the patient after the trialing period is completed. An electrical stimulator may deliver electrical stimulation therapy to a tongue of the patient via the one or more electrodes of the medical lead to cause the tongue to protrude for treating obstructive sleep apnea (OSA).

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIGS. 9A-9B are perspective drawings illustrating leads with fixation member(s) activated by a sheath removal.

DETAILED DESCRIPTION

Figure 1:
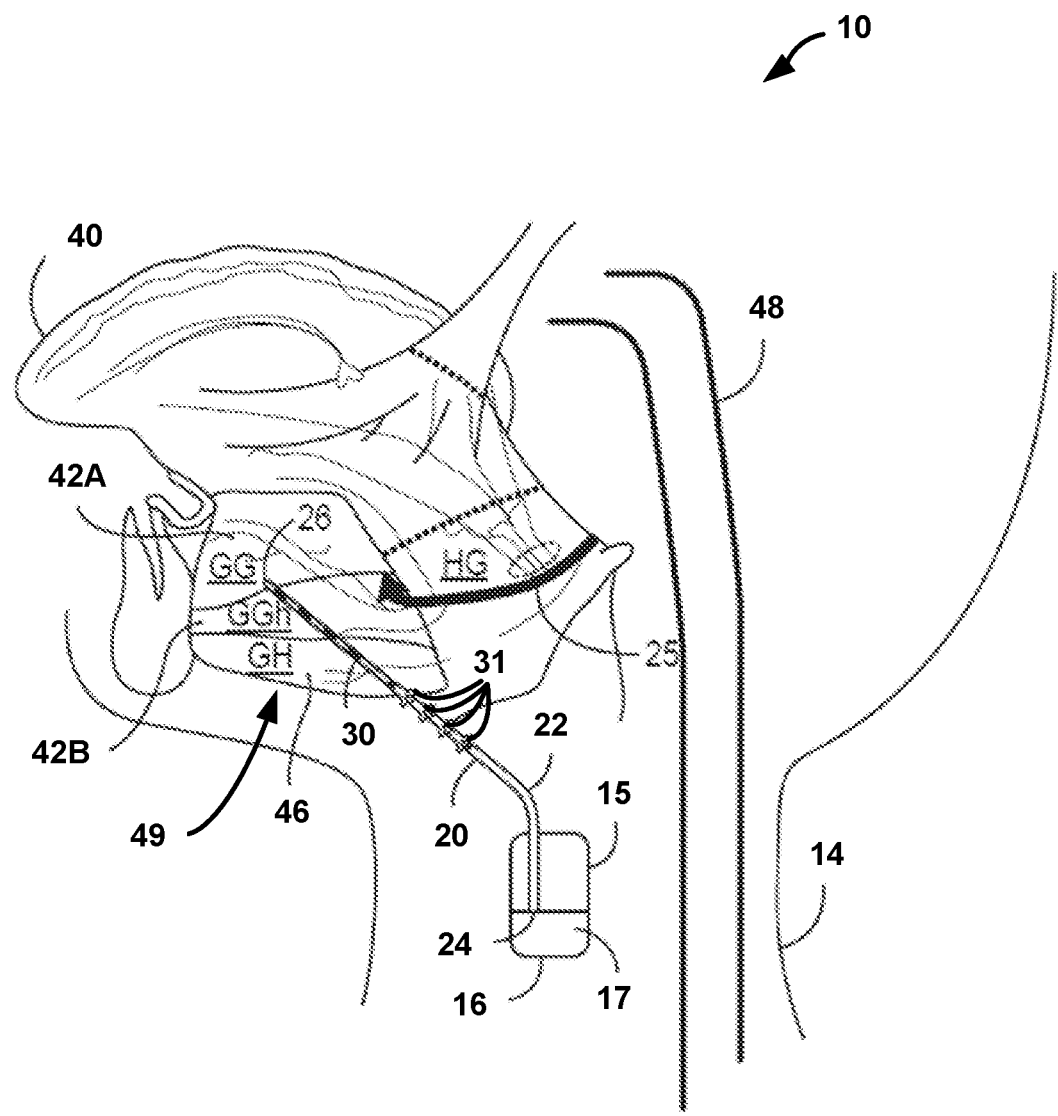
FIG. 1 is a conceptual diagram of an implantable medical device (IMD) system for delivering obstructive sleep apnea (OSA) therapy.

Medical devices, systems, and techniques for delivering electrical stimulation to the protrusor muscles of the tongue for the treatment of obstructive sleep apnea (OSA) are described in this disclosure. Electrical stimulation is delivered to cause the tongue of a patient to enter a protruded state, during sleep, to avoid or reduce upper airway obstruction. As used herein, the term, "protruded state" with regard to the tongue refers to a position that is moved forward and/or downward compared to a non-stimulated position or a relaxed position of the tongue. The protruded state is a state associated with contraction (e.g., via innervation from nerves in response to electrical stimulation) of protrusor muscles of the tongue (also sometimes referred to as "protruder" muscles of the tongue) including the genioglossus and geniohyoid muscles. A protruded state may be the opposite of a retracted and/or elevated position associated with the contraction of the retractor muscles (e.g., styloglossus and hyoglossus muscles) which retract and elevate the tongue. Electrical stimulation is delivered to cause the tongue to move (e.g., by depolarizing the nerve(s) that innervate the genioglossus and/or geniohyoid muscles) to and maintain a protruded state. As discussed above, the protruded state may prevent collapse or blockage of, open, or widen the upper airway of a patient to at least partially maintain or increase airflow (e.g., promote unrestricted airflow or at least reduced restriction of airflow during breathing).

A surgeon implants one or more leads that each include one or more electrodes into the tongue such that the electrodes are proximate to a hypoglossal nerve and/or motor points (e.g., one or more locations where axons of the hypoglossal nerve terminate at respective muscle fibers of the protrusor muscles). For example, there are two hypoglossal nerves in the tongue of the patient. In one example, one lead may be used to stimulate (e.g., by delivering electrical stimulation through one or more electrodes of the lead) one of the two hypoglossal nerves, one lead may be used to stimulate both hypoglossal nerves, or two leads may be used, where each lead stimulates a respective one of the hypoglossal nerves. Stimulation of either or both hypoglossal nerves of the tongue may cause contraction of the protrusor muscles to reduce the effect of or prevent, OSA.

There are multiple sets of motor points for each of the protrusor muscles on the left side and the right side. Each motor point may innervate one or more muscle fibers of the protrusor muscle. In one example, one lead may be used to stimulate motor points for the protrusor muscles on one side of the tongue, one lead may be used to stimulate motor points for protrusor muscles on both sides of the tongue, or two leads may be used, where each lead stimulates a respective set of motor points for the protrusor muscles on each side. Stimulation of either or both sets of motor points of the tongue can cause contraction of the protrusor muscles to reduce the effect of, or prevent, OSA.

This disclosure describes examples of techniques related to implantation of the one or more leads in the tongue for treatment of OSA. Although the example techniques are described with respect to OSA, the example techniques should not be construed as limited to OSA. Rather, the example techniques described in this disclosure may be applicable to lead implantation for treatment of various conditions including lead implantation for treatment of conditions where the lead is implanted in a location other than the tongue.

Before medical leads are implanted to provide stimulation therapy, a candidate trialing procedure is performed. This procedure is aimed at determining whether a patient is a good candidate to have an implantable lead implanted and used to provide stimulation therapy. A trialing period may also be used to determine stimulation parameters and location of the lead. For example, a sensitivity analysis and a determination of a baseline therapy parameter set may be performed as part of a trialing process. In such processes, an external trial therapy device (although an implanted trial therapy device is possible), such as a trial stimulator, may perform the functions ascribed to an IMD associated with performing the sensitivity analysis and determination of a baseline therapy parameter set. An IMD may then be implanted in a patient and programmed to deliver therapy according to the baseline therapy parameter set.

Separate surgeries are required for removing the trailing lead and implanting a chronic lead, which presents an infection risk. Additionally, prevention of tine deployment is desired during the trial period to provide ease of explanting the trialing lead.

The example techniques described in this disclosure may provide for both a trialing lead and a chronic lead. Example techniques described below provide for a lead which is used in the trailing process and when the trialing process is complete and the lead is in a chronic placement, the trialing lead may be made a chronic lead and implanted for long-term use. Example techniques include a sheath for an implantable lead which prevents tines on the implantable lead from deploying during the trialing procedure. The sheath may then be removed, and the tines are deployed to anchor the implantable lead for chronic use.

FIG. 1 is a conceptual diagram of a medical system for delivering OSA therapy. In system 10, implantable medical device (IMD) 16 and lead 20 are implanted in patient 14. IMD 16 includes housing 15 enclosing circuitry of IMD 16. In some examples, IMD 16 includes connector assembly 17, which is hermetically sealed to housing 15 and includes one or more connector bores for receiving a proximal end of at least one medical electrical lead 20 used for delivering OSA therapy. Although one lead 20 is illustrated in FIG. 1, there may be one or more leads 20 to which IMD 16 is coupled.

Lead 20 may include a flexible, elongate lead body 22, also called elongated member 22, that extends from lead proximal end 24 to lead distal end 26. As illustrated, lead 20 includes one or more electrodes 30 carried along a lead distal portion adjacent lead distal end 26 and are configured for insertion within the protrusor muscles 42A, 42B, and 46 of tongue 40. As one example, the genioglossus muscle includes oblique compartment 42A and horizontal compartment 42B. In this disclosure, the genioglossus muscle is referred to as protrusor muscle 42. Protrusor muscle 46 is an example of the geniohyoid muscle.

As illustrated, distal end 26 of lead 20 includes one or more electrodes 30. Proximal end 24 of lead 20 includes one or more electrical contacts to connect to connector assembly 17. Lead 20 also includes conductors such as coils or wires connecting respective electrodes 30 to respective electrical contacts at proximal end 24 of lead 20.

While protrusor muscles 42 and 46 are described, the example techniques described in this disclosure are not limited to stimulating protrusor muscles 42 and 46. Also, FIG. 1 illustrates one set of protrusor muscles 42 and 46 (e.g., on a first side of tongue 40). The other side of tongue 40 also includes protrusor muscles. For instance, a left side of tongue 40 includes a first set of protrusor muscles 42 and 46, and a right side of tongue 40 includes a second set of protrusor muscles.

In some examples, a surgeon may implant one or more leads 20 such that one or more electrodes 30 are implanted within soft tissue, such as musculature, proximate to medial branches of one or both hypoglossal nerves. In some examples, one or more electrodes 30 may be approximately 5 mm (e.g., 2 mm to 8 mm) from a major trunk of the hypoglossal nerve. In some examples, one or more electrodes 30 may be placed in an area of protrusor muscles 42 and 46 including motor points, where each nerve axon terminates in the muscle (also called the neuro-muscular junction). The motor points are not at one location but spread out in the protursor muscles. Leads 20 may be implanted so one or more electrodes 30 may be generally in the area of the motor points (e.g., so the motor points are within 1 to 10 mm from one or more electrodes 30). Examples of motor points for protrusor muscles 42 and 46 are illustrated in more detail with respect to FIG. 3.

Tongue 40 includes a distal end (e.g., tip of tongue 40), and electrodes 30 may be implanted proximate to root 49 of tongue 40. The surgeon may implant one or more leads 20 such that one or more electrodes are implanted proximate to root 49 of tongue 40, as illustrated in FIG. 1. For example, the location for stimulation for genioglossus muscle 42 may be approximately 30 mm (e.g., 25 mm to 35 mm) from the Symphsis of the jaw (e.g., where the genioglossus and hypoglossal muscles insert). The location for stimulation for geniohyoid muscle 46 may be approximately 40 mm (e.g., 35 mm to 45 mm) from the Symphsis. For both genioglossus muscle 42 and geniohyoid muscle 44, the location for stimulation may be approximately 11 mm (e.g., 7 mm to 15 mm) lateral to the midline on both the right and left sides of tongue 40 for stimulating respective hypoglossal nerves. In some examples, rather than stimulating hypoglossal nerves, the examples described in this disclosure may be configured for stimulating the motor points, as described in more detail with respect to FIG. 3. Stimulating the motor points may result in indirect activation of the hypoglossal nerve, but may generally be stimulating at a different location than direct stimulation to the hypoglossal nerve. As a result, in some examples, simulation of one or more motor points may result in more precise activation of muscle fibers than may be possible with stimulation of the hypoglossal nerve itself.

One or more electrodes 30 of lead 20 may be ring electrodes, segmented electrodes, partial ring electrodes or any suitable electrode configuration. Ring electrodes extend 360 degrees around the circumference of the lead body of lead 20. Segmented and partial ring electrodes each extend along an arc less than 360 degrees (e.g., 90-120 degrees) around the outer circumference of the lead body of lead 20. In this manner, multiple segmented electrodes may be disposed around the perimeter of lead 20 at the same axial position of the lead. In some examples, segmented electrodes may be useful for targeting different fibers of the same or different nerves at respective circumferential positions with respect to the lead to generate different physiological effects (e.g., therapeutic effects), permitting stimulation to be oriented directionally. In some examples, lead 20 may be, at least in part, paddle shaped (e.g., a "paddle" lead), and may include an array of electrodes arranged as contacts or pads on a common surface, which may or may not be substantially flat and planar.

As described above, in some examples, electrodes 30 are within musculature of tongue 40. Accordingly, one or more electrodes 30 may be "intramuscular electrodes." Intramuscular electrodes may be different than other electrodes placed on or along a nerve trunk or branch, such as a cuff electrode, used to directly stimulate the nerve trunk or branch. The example techniques described in this disclosure are not limited to intramuscular electrodes and may be extendable to electrodes placed closer to a nerve trunk or branch of the hypoglossal nerve(s). Also, in some examples, rather than one or more electrodes 30 being "intramuscular electrodes," one or more electrodes 30 may be implanted in connective tissue or other soft tissue proximate to the hypoglossal nerve.

In some examples, lead 20 may be configured for advancement through the soft tissue, which may include the protrusor muscle tissue, to anchor electrodes 30 in proximity to the hypoglossal nerve(s) innervating protrusor muscles 42 and/or 46 and/or motor points that connect axons of hypoglossal nerve(s) to respective muscle fibers of protrusor muscles 42 and/or 46. However, in some examples, lead 20 may be configured for advancement through vasculature of tongue 40. As one example, a surgeon may implant lead 20 in the lingual veins near the hypoglossal nerve though venous access in the subclavian vein. In such examples, one or more electrodes 30 may be "intravascular electrodes."

As described above, electrical stimulation therapy generated by IMD 16 and delivered via one or more electrodes 30 may activate protrusor muscles 42 and 46 to move tongue 40 forward, for instance, to promote a reduction in obstruction or narrowing of the upper airway 48 during sleep. As used herein, the term "activated" with regard to the electrical stimulation of protrusor muscles 42 and 46 refers to electrical stimulation causing depolarization or an action potential of the cells of the nerve (e.g., hypoglossal nerve(s)) or stimulation at the neuro-muscular junction between the nerve and the protrusor muscles (e.g., at the motor points) innervating protrusor muscles 42 and 46 and motor points and subsequent depolarization and mechanical contraction of the protrusor muscle cells of protrusor muscles 42 and 46. In some examples, protrusor muscles 42 and 46 may be activated directly by the electrical stimulation therapy.

Protrusor muscles 42 and/or 46, on a first side of tongue 40 (e.g., the left or right side of tongue 40), may be activated by a medial branch of a first hypoglossal nerve, and the protrusor muscles, on a second side of tongue 40 (e.g., the other of the left or right side of tongue 40), may be activated by a medial branch of a second hypoglossal nerve. The medial branch of a hypoglossal nerve may also be referred to as the XIIth cranial nerve. The hyoglossus and styloglossus muscles (not shown in FIG. 1), which cause retraction and elevation of tongue 40, are activated by a lateral branch of the hypoglossal nerve.

One or more electrodes 30 may be used to deliver bilateral or unilateral stimulation to protrusor muscles 42 and 46 via the medial branch of the hypoglossal nerve or branches of the hypoglossal nerve (e.g. such as at the motor point where a terminal branch of the hypoglossal nerve interfaces with respective muscle fibers of protrusor muscles 42 and/or 46). For example, one or more electrodes 30 may be coupled to output circuitry of IMD 16 to enable delivery of electrical stimulation pulses in a manner selectively activating the right and left protrusor muscles (e.g., in a periodic, cyclical or alternating pattern) to avoid muscle fatigue while maintaining upper airway patency. Additionally, or alternatively, IMD 16 may deliver electrical stimulation to selectively activate protrusor muscles 42 and/or 46 or portions of protrusor muscles 42 and/or 46 during unilateral stimulation of the left or right protrusor muscles.

In some examples, one lead 20 may be implanted so one or more of electrodes 30 deliver electrical stimulation to stimulate the left hypoglossal nerve or motor points of protrusor muscles on the left side of tongue, and therefore cause the left protrusor muscles to activate. In such examples, the electrical stimulation from one or more electrodes 30 may not be of sufficient amplitude to stimulate the right hypoglossal nerve or motor points of protrusor muscles on the left side of tongue and cause the right protrusor muscles to activate. In some examples, one lead 20 may be implanted so one or more of electrodes 30 deliver electrical stimulation to stimulate the right hypoglossal nerve or motor points of protrusor muscles on the left side of tongue, and therefore cause the right protrusor muscles to activate. In such examples, the electrical stimulation from one or more electrodes 30 may not be of sufficient amplitude to stimulate the left hypoglossal nerve or motor points of protrusor muscles on the left side of tongue and cause the left protrusor muscles to activate. Accordingly, in some examples, two leads like lead 20 may be implanted to stimulate each of the left and right hypoglossal nerves and/or motor points of respective protrusor muscles on the left and right side of tongue 40.

In some examples, one lead 20 may be implanted substantially in the middle (e.g., center) of tongue 40. In such examples, one or more electrodes 30 may deliver electrical stimulation to both hypoglossal nerves or motor points of both muscles on the both sides of tongue 40 causing both hypoglossal nerves or motor points to activate respective left and right protrusor muscles. It may be possible to utilize current steering and field shaping techniques so one or more electrodes 30 deliver first electrical stimulation stimulating the left hypoglossal nerve or motor points of protrusor muscles on the left side of tongue 40 with little to no stimulation of the right hypoglossal nerve or motor points of protrusor muscles on the right side of tongue 40, and then one or more electrodes 30 deliver second electrical stimulation stimulating the right hypoglossal nerve or motor points of protrusor muscles on the right side of tongue with little to no stimulation of the left hypoglossal nerve or motor points of protrusor muscles on the left side of tongue. In examples where two leads like lead 20 are utilized, each lead may alternate delivery of stimulation to respective hypoglossal nerves or motor points. In this way, IMD 16 may stimulate one hypoglossal nerve or one set of motor points and then the other hypoglossal nerve or another set of motor points, which may reduce muscle fatigue.

For instance, continuous stimulation may cause protrusor muscles to be continuously in a protruded state. This continuous contraction may cause protrusor muscles 42 and/or 46 to fatigue. In such cases, due to fatigue, the stimulation may not cause protrusor muscles 42 and/or 46 to maintain a protruded state (or higher intensity of the electrical stimulation may be needed to cause protrusor muscles 42 and/or 46 to remain in the protruded state). By stimulating one set of protrusor muscles (e.g., left or right) a second set (e.g., other of left or right) of protrusor muscles may be at rest. Stimulation may then alternate to stimulate the protrusor muscles which were at rest and thereby maintain protrusion of tongue 40, while permitting the protrusor muscles 42 and/or 46 previously activated to rest. Hence, by cycling between alternate stimulation of the left and right protrusor muscles, tongue 40 may remain in the protruded state, while one of the first or second set of protrusor muscles is at rest.

In some examples, one lead 20 may be implanted laterally or diagonally across tongue 40 so some of electrodes 30 on lead 20 may be used to stimulate the left hypoglossal nerve and/or motor points of the protrusor muscles on the left side of tongue 40 and some of electrodes 30 on the same lead 20 may be used to stimulate the right hypoglossal nerve and/or motor points of the protrusor muscles on the right side of tongue 40. In such examples, IMD 16 may selectively deliver electrical stimulation to a first hypoglossal nerve and/or first motor points of the protrusor muscles on a first side of tongue 40 via a first set of one or more electrodes 30, and then deliver electrical stimulation to a second hypoglossal nerve and/or second set of motor points of the protrusor muscles on a second side of tongue 40 via a second set of one or more electrodes 30. This may be another way in which to reduce muscle fatigue.

Lead proximal end 24 includes a connector (not shown in FIG. 1) may be coupled to connector assembly 17 of IMD 16 to provide electrical connection between circuitry enclosed by housing 15 of IMD 16. Lead body 22 encloses electrical conductors extending from each of one or more electrodes 30 to the proximal connector at proximal end 24 to provide electrical connection between output circuitry of IMD 16 and the electrodes 30.

There may be various ways in which lead 20 is implanted in patient 14. As one example, a surgeon may insert a needle (also called introducer needle) through the lower part of the jaw and in tongue 40 starting from the back of tongue 40. The surgeon may insert the needle until a distal tip of the needle reaches a point at or adjacent to the tip of tongue 40, angling the needle to extend proximate to the hypoglossal nerve (e.g., left or right hypoglossal nerve) and to the motor points. In some examples, the needle may include one or more electrodes (e.g., one to four electrodes) at the distal end, and the surgeon may cause the one or more electrodes of the needle to output electrical stimulation (e.g., in the form of controlled current pulses or controlled voltage pulses), which in turn causes a physiological response such as activation of protrusor muscles 42 and/or 46 and protrusion of tongue 40. The surgeon may adjust the location of the needle based on the physiological response to determine a location in tongue 40 providing effective treatment. Using a needle with stimulating electrodes is not necessary in every example.

Once the needle is in place, the surgeon may insert a guidewire (or simply "guide") through the needle and anchor the guidewire (e.g., with tines on the guidewire) to tissue of tongue 40. Then, the surgeon may remove the needle, leaving behind the guidewire.

The surgeon may place an introducer, which may or may not include a dilator, over the guidewire through the opening created by the needle. The introducer may be referred to as an introducer, introducer sheath, or introducer/dilator. In some examples, the introducer may optionally include one or more electrodes the surgeon may use to test stimulation of tongue 40 to ensure lead 20 will be located in the correct location, relative to the target nerve tissue (e.g., motor points). Once the introducer is in place, the surgeon may remove the guidewire. In some examples, the introducer may be flexible or curved to ease placement of the introducer in patient 14.

The surgeon may prepare lead 20 for insertion. In some examples, there may be an additional sheath placed over lead 20 holding fixation member(s), such as those described with respect to FIGS. 2, 8A and 8B in place. Use of such an additional sheath is not necessary in all examples. Because lead 20 may be highly flexible, in some examples, the surgeon may place a stylet through lead 20 to provide some rigidity and allow lead 20 to traverse through tongue 40 under a pushing force. Use of a stylet may not be necessary in all examples.

The surgeon may put lead 20 through the introducer so one or more electrodes 30 are proximate to the hypoglossal nerve (e.g., so distal end 26 is near tip of tongue as one non-limiting example). Electrodes 30 may be proximate to the hypoglossal nerve and/or motor points of the protrusor muscles due to the needle creating an opening near the hypoglossal nerve and/or motor points of the protrusor muscle. The surgeon may then tunnel proximal end 24 of lead 20 back to a connection with IMD 16.

In this manner, the surgeon may implant one lead 20. In examples where two or more leads are implanted, the surgeon may perform steps similar to those described above.

The above describes some example techniques for lead placement, and the examples described in this disclosure should not be considered limited to such examples of lead placement. Moreover, in some examples, the surgeon may use imaging techniques, such as fluoroscopy, during implantation to verify proper placement of lead 20, the needle, and/or the introducer.

FIG. 1 illustrates the location of IMD 16 as being within or proximate to the neck of patient 14. However, IMD 16 may be implanted in various other locations. As one example, the surgeon may implant IMD 16 in the left or right pectoral region. For instance, the surgeon may plan on implanting IMD 16 in the left pectoral region unless another medical device is already implanted in the left pectoral region. If another medical device is already implanted in the left pectoral region, the surgeon may then implant IMD 16 in the right pectoral region. There may be other locations where the surgeon may implant IMD 16 such as the back of patient 14. The example techniques are not limited to any particular implant location of IMD 16.

In accordance with one or more examples described in this disclosure, a combination trialing and chronic implantable lead having a fixation member reduces the number of implant procedures, thus reducing a patient's infection risk Further, the trialing and chronic lead do not have to be moved once placed. This prevents the implanting clinician from not being able to reproduce the positioning of the trialing lead after it is removed and the chronic lead is implanted. Often, the electrode position of the trialing lead may not be exactly reproduced with the chronic lead. Leaving the trialing lead in place ensures the response to stimulation will not change due to a different electrode position with the implantation of a chronic lead. In examples described in this disclosure an implantable lead is provided with a sheath which prevents the fixation members from adhering to the patient. Thus, during a trialing phase, the implantable lead may be moved and tested to find an optimum location within protrusor muscles 42 and/or 46 to provide OSA therapy. In examples described in this disclosure, the sheath may be removed from the implantable lead when it is desired to move from a trialing period to a chronic use of the implantable lead. The lead is fully useful during the trialing period as electrodes are exposed to the patient as the electrodes may be in chronic use. For purposes of examples of this disclosure, chronic may be defined as long-term therapy using an implanted medical device.

However, the fixation members are covered until the trialing period is over. Thus, a trialing lead does not need to be removed and a chronic lead implanted. The chronic lead is already implanted and may be fastened to the patient by simply removing the sheath covering the fixation member. In examples of the disclosure, the sheath is something which should stay in place for multiple hours (i.e., a trialing period may be more than a few hours such as during the time the patient is sleeping) and is not removed during the initial implantation surgery. In examples of the disclosure, the sheath may have an adaptor which allows a clinician to unsecure the sheath from the implantable lead, which allows for the sheath to be removed when it is desired to end the trialing phase and make the implantable lead a chronic implantable lead. Further, the sheath and adaptor may operate separately. A proximal end of the adaptor may provide a percutaneous connection to the trial stimulator (e.g., external stimulator used for the trialing period). Then, the proximal end of the lead is disconnected from the adaptor and connected into the chronic implantable device. The proximal end has connectors that fit into the chronic implantable device.

Figure 2:
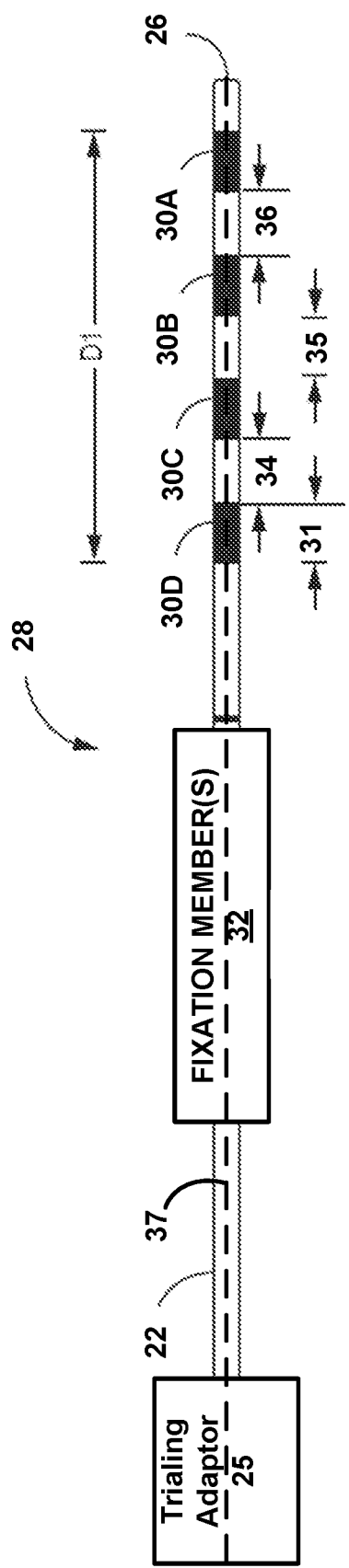
FIG. 2 is a conceptual diagram of a lead used for OSA therapy according to one or more examples of this disclosure.

FIG. 2 is a conceptual diagram of lead 20 used for OSA therapy according to one or more examples. For instance, FIG. 2 illustrates distal portion 28 of lead 20, where distal portion 28 of lead 20 may form part of lead 20 implanted in tongue 40, as described above. Lead 20 may include one or more electrodes 30, and FIG. 2 shows lead 20 with four electrodes 30A, 30B, 30C, and 30D (collectively referred to as "electrodes 30") spaced apart longitudinally along lead body 22. Lead body 22 is an example of the elongated member of lead 20. For instance, lead body 22 and the elongated member of lead 20 are the same.

Lead body 22 (e.g., elongated member of lead 20) may be a flexible lead body through which insulated electrical conductors extend to respective electrodes 30. The distal most electrode 30A may be adjacent or proximate to lead distal end 26. Each of electrodes 30 may be spaced proximally from the respective adjacent one of electrodes 30 by respective interelectrode distances 34, 35 and 36.

The electrical conductors extending to respective electrodes 30 from proximal contacts at proximal end 24 may be arranged as a plurality of coils. The coils may increase the flexibility of lead 20 so lead 20 can bend at the distal end. In some examples, the coils may be exposed along the locations of electrodes 30 so the coils form electrode 30. Rather than electrodes 30 being pad electrodes or ring electrodes, the coils form electrodes 30 and, in this way, electrodes 30 are bendable, providing additional flexibility. In such examples, electrodes 30 are coil electrodes.

In some examples, each one of electrodes 30 may have equivalent electrode lengths 31 (e.g., longitudinal extend of electrodes 30 along lead body 22). Lengths 31 may be approximately 3 mm, but less than 3 mm lengths are possible. However, electrodes 30 may have electrode lengths 31 different from each other in order (e.g., to optimize placement of electrodes 30 or the resulting electrical field of stimulation relative to targeted stimulation sites corresponding to left and right hypoglossal nerves or branches of hypoglossal nerves and/or motor points of protrusor muscles 42 and/or 46).

Spacing 34, 35, and 36 are shown to be approximately equal in FIG. 2. However in other examples interelectrode spacings 34, 35, and 36 may be different from each other (e.g., in order to optimize placement of electrodes 30 relative to the targeted stimulation sites). Spacing 34, 35 and 36 may be approximately 3 mm but less than 3 mm spacing is possible. In some examples, for bipolar configuration, electrodes 30A and 30B form an anode and cathode pair for delivering bipolar stimulation in one portion of protrusor muscles 42 and/or 46 (e.g., either the left or right protrusor muscles or a proximal and/or distal portion the protrusor muscles). Electrodes 30C and 30D may form a second anode and cathode pair for delivering bipolar stimulation in a different portion of protrusor muscles 42 and/or 46 (e.g., the other of the left or right portions or the other of the proximal or distal portions). Accordingly, interelectrode spacing 35 between two bipolar pairs 30A, 30B and 30C, 30D may be different than interelectrode spacing 34 and 36 between the anode and cathode within each bipolar pair 30A, 30B and 30C, 30D.

In some examples, for a unipolar configuration housing 15 of IMD 16 may include an electrode functioning as cathode, and part of the anode and cathode pair with one of electrodes 30. In some examples, housing 15 itself may function as the cathode of an anode, cathode pair, with one of electrodes 30 forming the anode. Housing 15 may be anode in some examples.

In one example, the total distance D1 encompassed by electrodes 30 along distal portion 28 of lead body 22 may be between 20 and 30 millimeters. In one example, the total distance D1 is between approximately 20 and 22 millimeters. However, as an alternative, the distances may be shorter. As one example, the distance from distal portion 28 to one or more fixation members 32 may be approximately 10 mm to ensure at least on of the one or more fixation member(s) 32 is implanted within tongue 40.

The interelectrode spacings 34 and 36 within a proximal electrode pair 30C, 30D and a distal electrode pair 30A, 30B, respectively, may be in a range of approximately 2 to 5 millimeters in some examples. Interelectrode spacing 35 separating distal and proximal pairs 30A, 30B and 30C, 30D may be greater than interelectrode spacings 34 and 36. For example, interelectrode spacing 35 may be in the range of approximately 4 to 6 millimeters in some examples. In one example, each of electrodes 30 has an electrode length 31 of approximately 3 mm, and each of interelectrode spacings 34, 35 and 36 is approximately 3 mm.

In FIG. 2, each of electrodes 30 is a circumferential ring electrode which may be uniform in diameter with lead body 22. As described above, electrodes 30 may include other types of electrodes such as a tip electrode, a helical electrode, a coil electrode, as described above, a segmented electrode, a button electrode as examples. For instance, the distal most electrode 30A may be provided as a tip electrode at the lead distal end 26 with the remaining three electrodes 30B, 30C, and 30D being ring electrodes. In some examples, when electrode 30A is positioned at distal end 26, electrode 30A may be a helical electrode configured to screw into the muscle tissue at the implant site to additionally serve as a fixation member for anchoring the distal portion 28 of lead 20 at the targeted therapy delivery site. In some examples, one or more of electrodes 30 may be a hook electrode or barbed electrode to provide active fixation of distal portion 28 of lead 20 at the therapy delivery site.

Lead 20 may include one or more fixation members 32 for minimizing the likelihood of lead migration. Fixation member 32 may include multiple sets of tines which engage the surrounding tissue when lead distal portion 28 is positioned at the target therapy delivery site. The tines of fixation member 32 may extend radially outward and proximally at an angle relative to a longitudinal axis 37 of lead body 22 to prevent or reduce retraction of lead body 22. For instance, the tines may include springs in an uncompressed state extending the tines outwards. Tines of fixation member 32 may be collapsible against lead body 22 when lead 20 is held within the confines of a lead delivery tool (e.g., a needle or introducer) used to deploy lead distal portion 28 at the target implant site. Upon removal of the lead delivery tool, and as discussed in another example below a sheath 100 (FIG. 6), the tines of fixation member 32 may spread to a normally extended position (e.g., due to the spring bias) to engage with surrounding tissue and resist proximal and lateral migration of lead body 22. For instance, the tines may be normally biased to the extended position but retracted against the introducer for implantation. When the introducer is removed, the tines extend outward to their uncompressed state. Examples of the tines for fixation members 32 include tines 31 of FIG. 1. In some examples, fixation member 32 may additionally or alternatively include one or more hooks, barbs, helices, or other fixation mechanisms extending from one or more longitudinal locations along lead body 22 and/or lead distal end 26.

In some examples, the tines, when deployed, may be forward facing and/or backward facing. Forward facing means the portion of the tines more proximate to proximal end 24 spread out when deployed. For instance, the tine has a connection point on lead body 22 and free arm of the tine extends away from the lead body 22, and the portion of the free arm more proximate to proximal end 24 extends. Backward facing means the portion of the tines more proximate to distal end 26 spread out when deployed. For instance, the tine has a connection point on lead body 22 and a free arm of the tine extends away from lead body 22, and the portion of the free arm more proximate to distal end 26 extends. Having both forward and backward facing tines may reduce lateral and proximal migration.

Fixation members 32 may partially or wholly engage one or more of protrusor muscles 42 and/or 46 and/or other muscles below tongue 40, and/or other soft tissues of the neck (e.g., fat and connective tissue), when proximal end of lead body 20 is tunneled to an implant pocket of IMD 16. In some examples, fixation member 32 may include one or more fixation mechanisms located at other locations, including at or proximate to distal end 26, between electrodes 30, or otherwise more distally or more proximally than the location shown in FIG. 2.

The implant pocket of IMD 16 may be in a pectoral region of patient 14. Lead body 22 may include proximal connectors engaging with connector assembly 17 of IMD 16. Accordingly, the length of lead body 22 from distal portion 28 to lead proximal end 24 may be selected to extend from a target therapy delivery site in protrusor muscles 42 and/or 46 to a location in the pectoral region where IMD 16 is implanted. The length of lead body 22 (e.g., elongated member) may be up to 10 cm or up to 20 cm as examples but may generally be 25 cm or less, though longer or shorter lead body lengths may be used depending on the anatomy and size of patient 14.

In some examples, an IMD 16 having a lead 20 with a proximal end 24 and a distal end 26 defines an elongated lead body 22 with electrodes 30 disposed on lead 20. In some examples, lead 20 provides for a combination trialing lead and chronic lead. In other examples, a fixation member 32 may be disposed on elongated lead body 22 of lead 20. Fixation member 32 may be configured to secure lead 20 to tissue within a patient 14. Fixation member 32 may be disposed on lead 20 at a location proximal to electrodes 30 of lead 20. In some examples, separate surgeries for implantation of a trialing lead and a chronic lead are reduced to one surgery for a combination trialing and chronic lead. Once the lead is placed in a location proven effective for OSA stimulation, a sheath 100 (FIG. 6), configured to enclose at least a portion of lead 20 and cover fixation member 32 may be removed, thus exposing fixation member 32 to the patient's tissue and fixating lead 20. A locking head 108 (FIG. 6) on the proximal end of sheath 100 may assist in retaining sheath 100 on elongated lead body 22 for extended periods of time during the trialing period and may be removed when a clinician chooses to end the trialing period and convert implantable lead 20 from a trialing lead to a chronic implantable lead.

After surgery during the stimulation trial, a trial system may employ a lead 20, which is connected to a trialing adaptor 25 (FIG. 2.) connected to a trial stimulator worn externally on clothing or a lanyard. Proximal end 24 of lead 20 is both electrically and mechanically coupled to a trial stimulator via trialing adaptor 25. Trialing adaptor 25, which may be configured to connect a number of different types of leads to a trial stimulator. Trialing adaptor 25 may vary from the example illustrated in FIG. 2. For example, trialing adaptor 25 may be branched so it is configured to couple multiple percutaneous leads to a trial stimulator.

In one or more examples, trialing adaptor 25 provides an interface for percutaneous connection of the trial stimulator to lead 20. For example, proximal end 24 of lead 20 may include connectors, and trialing adaptor 25 may be connected to the connectors. A distal end of trialing adaptor 25 (e.g., end closer to electrodes 30) may be within the body of the patient, and a proximal end of trialing adaptor 25 (e.g., end closer to the skin of the patient) may exit from the body of the patient to provide a percutaneous connection to the trial stimulator for a duration of the trialing period.

After the trialing period, trialing adaptor 25 may be removed. The connectors at proximal end 24 of lead 20 may be connected to IMD 16. In this manner, there may not be a need to remove lead 20 after implantation for the trialing period, and the trialing lead may become the chronic lead.

In one example, trialing adaptor 25 may include, in addition to electrical connections for connecting lead 20 to a trial stimulator, an electrical contact configured to connect with a conductor of lead 20 in order to close a circuit configured to facilitate autonomous detection of the type of lead 20 connected to a trial stimulator. For example, trialing adaptor 25 may include an electrical contact connecting a conductor of lead 20 to a controlled current source included in a trial stimulator configured to deliver a particular amount of current across the lead conductor. The circuit with the controlled current source included in a trial stimulator may be configured to measure the voltage drop across the lead conductor.

In an example of the present disclosure, trialing adaptor 25 is removed when sheath 100 is removed and lead 20 converts from a trial lead to a chronic lead. Trailing adaptor 25 may be explanted when lead 20 is converted from a trialing lead to a chronic lead. Trialing adaptor 25 assists in preventing infections. Trailing adaptor 25 may be externalized to provide percutaneous connection to the external stimulation device (e.g., as described above, a portion of trailing adaptor 25 may be located inside a patient's body while a portion of trailing adaptor 25 is located outside of the patient's body for connection to a trailing stimulator).

Figure 3:
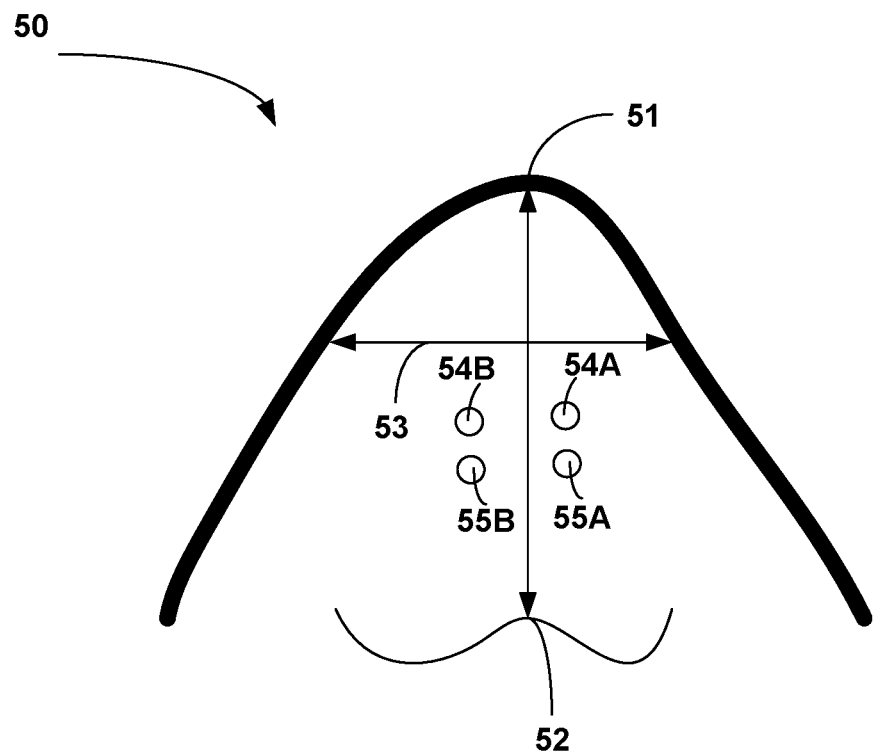
FIG. 3 is a conceptual diagram illustrating example locations of motor points where stimulation for OSA therapy may be delivered.

FIG. 3 is a conceptual diagram illustrating example locations of motor points where stimulation for OSA therapy may be delivered. FIG. 3 illustrates jaw 50 of patient 14, where patient 14 is in a supine position and jaw 50 of patient 14 is viewed from an inferior location of patient 14. For instance, FIG. 3 illustrates symphysis 51 and hyoid bone 52. In the example illustrated in FIG. 3, the line interconnecting symphysis 51 and hyoid bone 52 may be considered as a y-axis along the midline of tongue 40. FIG. 3 also illustrates intergonial distance 53 between the two gonia of patient 14, where the gonia is a point on each side of the lower jaw 50 at the mandibular angle. Intergonial distance 53 may be along the x-axis of tongue 40.

FIG. 3 illustrates motor points 54A and 54B and motor points 55A and 55B. Motor points 54A may be motor points for the right genioglossus muscle, and motor points 54B may be motor points for the left genioglossus muscle. Motor points 55A may be motor points for the right geniohyoid muscle, and motor points 55B may be motor points for the left geniohyoid muscle. Motor points 54A and 54B and motor points 55A and 55B may genericize the motor points for each muscle for purposes of illustration. There may be additional motor points and/or motor points at different locations for each muscle.

In one or more examples, lead 20 and/or one or more electrodes 30 may be implanted proximate to motor points 54A, 54B, 55A, or 55B for stimulating at motor points 54A, 54B, 55A, and/or 55B. For instance, in examples where two leads are implanted, a first lead and its electrodes may be implanted proximate to motor points 54A and/or 55A and a second lead and its electrodes may be implanted proximate to motor points 54B and/or 55B. In one or more examples, electrodes 30 may be approximately 1 mm to 10 mm from respective motor points 54A, 54B, 55A, or 55B.

A hypoglossal nerve (e.g., on the left or right side of tongue 40) initially is a trunk of nerves fibers called axons. The axons of the hypoglossal nerve branch out. For example, the trunk of hypoglossal nerve includes multiple sets of axons including a first set of axons, and the first set of axons branch out from the trunk of the hypoglossal nerve. The first set of axons include multiple groups of axons including a first group of axons, and the first group of axons branch out from the first set of axons, and so forth. The locations where the branched-out axons interface with respective muscle fibers of protrusor muscles 42 and/or 46 (e.g., genioglossus and/or geniohyoid muscle) are referred to as motor points.

For instance, a branch of the hypoglossal nerve that interfaces (e.g., connects at the neuro-muscular junction) with the muscle fiber is referred to as a terminal branch, and the end of the terminal branch is a motor point. The length of a terminal branch may be approximately 10 mm from the hypoglossal nerve to the genioglossal or geniohyoid muscles. In some examples, there may be approximately an average of 1.5 terminal branches with a standard deviation of +0.7 for the right geniohyoid muscle, an average of 4.8 terminal branches with a standard deviation of +1.4 for the right genioglossus muscle, an average of 2.0 terminal branches with a standard deviation of +0.9 for the left geniohyoid muscle, and an average of 5.1 terminal branches with a standard deviation of +1.9 for the left genioglossus muscle.

There may be possible advantages with stimulating at motor points 54A, 54B, 55A, or 55B, as compared to some other techniques. For instance, some techniques utilize cuff electrodes or stimulate at the hypoglossal nerve. Due to the different bifurcation patterns, placing a cuff electrode around the hypoglossal nerve, or generally attaching an electrode to the hypoglossal nerve can be challenging. Also, where cuff electrodes or electrodes that attach to the hypoglossal nerve are used, implanting electrodes around or at each of the hypoglossal nerves requires multiple surgical entry points to attached to both hypoglossal nerves. Moreover, utilizing cuff electrodes or electrodes that attach to the hypoglossal nerves can possibly negatively impact the nerve by tugging, stretching, or otherwise causing irritation. Accordingly, utilizing lead 20 and electrodes 30 that are implanted proximate to the motor points may be beneficial (e.g., less surgery to implant and less impact on the nerve) as compared to techniques where cuff electrodes or electrodes implanted on the hypoglossal nerve are utilized.

Furthermore, stimulating at motor points 54A, 54B, 55A, and/or 55B, such as at the bifurcation point of a motor neuron that attach to muscle fibers, may provide advantages such as for better control of muscle movement. Because motor points 54A, 54B, 55A, and 55B are spatially distributed, by stimulating motor points 54A, 54B, 55A, and/or 55B, the amount of the genioglossus and geniohyoid muscle that is being stimulated can be controlled. Also, stimulating at motor points 54A, 54B, 55A, and/or 55B may allow for more gentle muscle activation. For instance, when stimulation is provided near the trunk of the hypoglossal nerve, even stimulation signal with relatively small amplitude can cause the genioglossus and/or geniohyoid muscle to fully protrude (e.g., there is high loop gain where small stimulation amplitudes cause large muscle protrusion). Fine tuning of how much to protrude the genioglossus and/or geniohyoid muscle may not be available when stimulating at a trunk of the hypoglossal nerve. However, there may be lower loop gain stimulating at motor points 54A, 54B, 55A, and/or 55B. For instance, a stimulation signal having a lower amplitude may move cause the genioglossus and/or geniohyoid muscle to protrude a small amount, and a stimulation signal having a higher amplitude may move cause the genioglossus and/or geniohyoid muscle to protrude a higher amount when stimulating at motor points 54A, 54B, 55A and/or 55B.

The following are example locations of motor points 54A, 54B, 55A, and 55B relative to the midline (x-axis), posterior symphysis 51 (y-axis), and depth (z-axis), where the depth is from the plane formed by the inferior border of symphysis 51 and anterior border of hyoid bone 52.

Motor points 54A may be for the right genioglossus muscle and may be located at 13.48 mm±3.59 from the x-axis, 31.01 mm±6.96 from the y-axis, and 22.58 mm±3.74 from the z-axis. Motor points 55A may be for the right geniohyoid muscle and may be located at 11.74 mm±3.05 from the x-axis, 41.81 mm±6.44 from the y-axis, and 16.29 mm±3.40 from the z-axis. Motor points 54B may be for the left genioglossus muscle and may be located at 9.96 mm±2.24 from the x-axis, 29.62 mm±9.25 from the y-axis, and 21.11 mm±4.10 from the z-axis. Motor points 55B may be for the left geniohyoid muscle and may be located at 11.45 mm±1.65 from the x-axis, 39.63 mm±8.03 from the y-axis, and 15.09 mm±2.41 from the z-axis.

Figure 4:
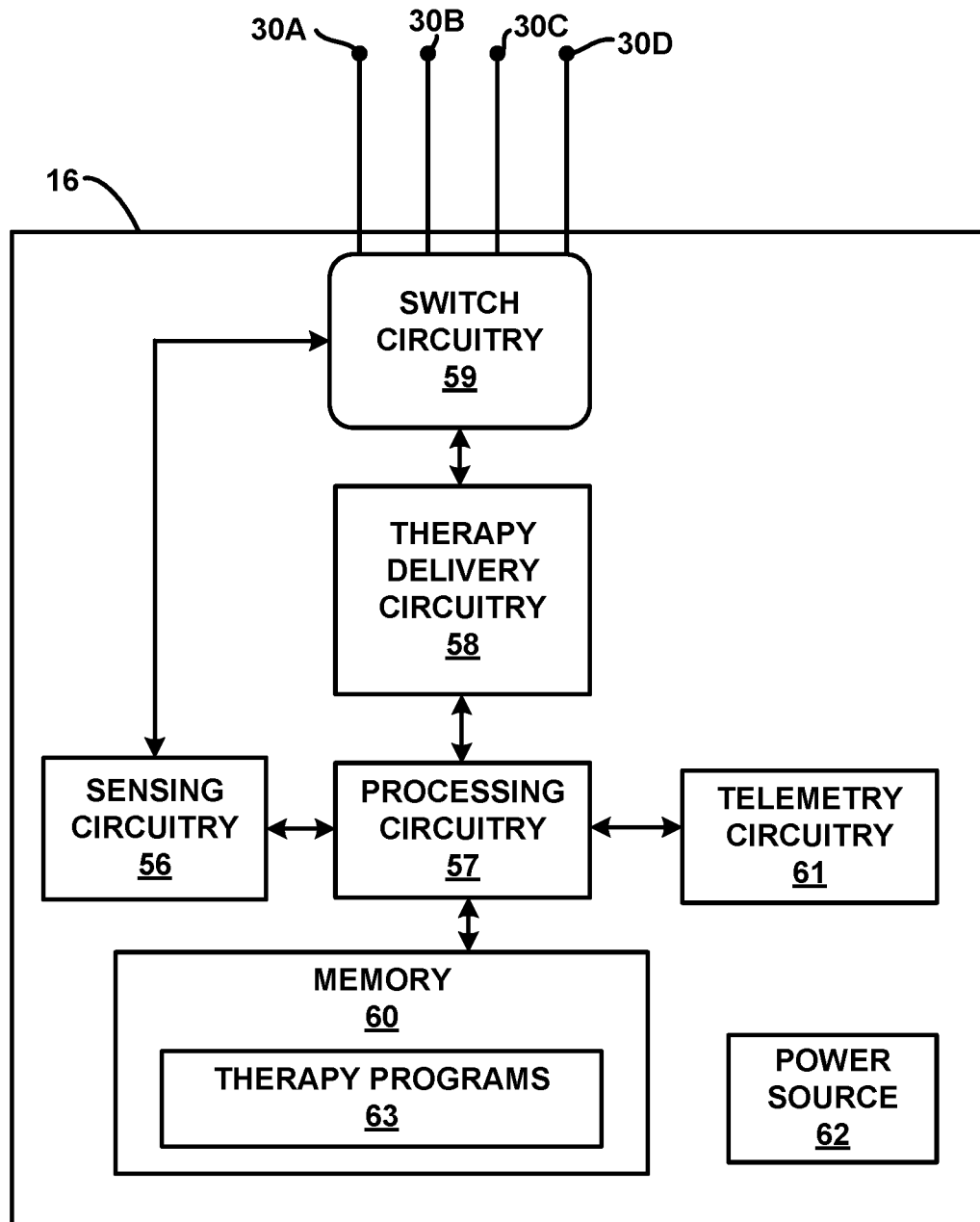
FIG. 4 is block diagram illustrating example configurations of implantable medical devices (IMDs) which may be utilized in the system of FIG. 1.

FIG. 4 is block diagram illustrating example configurations of implantable medical devices (IMDs) which may be utilized in the system of FIG. 1. As shown in FIG. 4, IMD 16 includes sensing circuitry 56, processing circuitry 57, therapy delivery circuitry 58, switch circuitry 59, memory 60, telemetry circuitry 61, and power source 62. IMD 16 may include a greater or fewer number of components. For example, in some examples, such as examples in which IMD 16 deliver the electrical stimulation in an open-loop manner, IMD 16 may not include sensing circuitry 56. IMD 16 may be used for chronic stimulation, but an external medical device may also be used for trialing, which may be similar to IMD 16, but need not necessarily be similar to IMD 16.

Switch circuitry 59 may be configured to, in response to instructions from processing circuitry 57, switch the coupling of electrodes 30 between sensing circuitry 56 and therapy delivery circuitry 58. In examples where sensing circuitry 56 is not used, switch circuitry 59 may not be needed. However, even in examples where sensing circuitry 56 is not used, IMD 16 may include switch circuitry 59 such as to disconnect electrodes 30 from therapy delivery circuitry 58.

In some examples, therapy delivery circuitry 58 may include a plurality of regulated current sources or sinks, with each current source or sink coupled to one of electrodes 30. In such examples, therapy delivery circuitry 58 may control each current source or sink and switching between electrodes 30 may not be necessary for therapy delivery since each one of electrodes 30 is individually controllable.

Although not shown in FIG. 4, in some examples, IMD 16 may include one or more sensors configured to sense posture or position of patient 14. For example, IMD 16 may include accelerometer to determine if patient 14 is lying down. Another example of the one or more sensors is a motion sensor, and movement sensed by the motion sensor may indicate if patient 14 is having restless sleep, which may be indicative of the onset of OSA. Additional examples of the sensors include acoustical sensors or a microphone for detecting vibrations in upper airway 48. Vibrations in upper airway 48 may be indicative of the onset of OSA. In some examples, processing circuitry 52 may control delivery of therapy based on information received from the one or more sensors, such as delivery therapy after sensing an onset of OSA.

In some examples, electrodes 30 may be configured to sense electromyogram (EMG) signals. Sensing circuitry 56 may be switchably coupled to electrodes 30 via switch circuitry 59 to be used as EMG sensing electrodes with electrodes 30 are not being used for stimulation. EMG signals may be used by processing circuitry 57 to detect sleep state and/or low tonal state of protrusor muscles 42 and/or 46 for use in delivering electrical stimulation. In some examples, rather than using electrodes 30 or in addition to using electrodes 30, there may be other electrodes or sensors used to sense EMG signals.

In general, IMD 16 may comprise any suitable arrangement of hardware, alone or in combination with software and/or firmware, to perform the techniques attributed to IMD 16 and processing circuitry 57, therapy delivery circuitry 58, and telemetry circuitry 61 of IMD 16. In various examples, IMD 16 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components.

The various units of IMD 16 may be implemented as fixed-function circuits, programmable circuits, or a combination thereof. Fixed-function circuits refer to circuits that provide particular functionality and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, one or more of the units may be distinct circuit blocks (fixed-function or programmable), and in some examples, one or more of the units may be integrated circuits.

IMD 16 may include arithmetic logic units (ALUs), elementary function units (EFUs), digital circuits, analog circuits, and/or programmable cores, formed from programmable circuits. In examples where the operations of IMD 16 are performed using software executed by the programmable circuits, memory 60 may store the instructions (e.g., object code) of the software that processing circuitry 52 receives and executes, or another memory within IMD 16 (not shown) may store such instructions.

IMD 16 also, in various examples, may include a memory 60, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although sensing circuitry 56, processing circuitry 57, therapy delivery circuitry 58, switch circuitry 59, and telemetry circuitry 61 are described as separate circuitry, in some examples, sensing circuitry 56, processing circuitry 57, therapy delivery circuitry 58, switch circuitry 59, and telemetry circuitry 61 are functionally integrated. In some examples, sensing circuitry 55, processing circuitry 57, therapy delivery circuitry 58, switch circuitry 59, and telemetry circuitry 61 correspond to individual hardware units, such as ASICs, DSPs, FPGAs, or other hardware units.

Memory 60 stores therapy programs 63 (also called stimulation programs 63) specifying stimulation parameter values for the electrical stimulation provided by IMD 16. Memory 60 may also store instructions for execution by processing circuitry 57, in addition to stimulation programs 62. Information related to sensed parameters of patient 14 (e.g., from sensing circuitry 56 or the one or more sensors of IMD 16) may be recorded for long-term storage and retrieval by a user, and/or used by processing circuitry 57 for adjustment of stimulation parameters (e.g., amplitude, pulse width, and pulse rate). In some examples, memory 60 includes separate memories for storing instructions, electrical signal information, and stimulation programs 62. In some examples, processing circuitry 57 may select new stimulation parameters for a stimulation program 62 or new stimulation program from stimulation programs 62 to use in the delivery of the electrical stimulation based on patient input and/or monitored physiological states after termination of the electrical stimulation.

Generally, therapy delivery circuitry 58 generates and delivers electrical stimulation under the control of processing circuitry 57. In some examples, processing circuitry 57 controls therapy delivery circuitry 58 by accessing memory 60 to selectively access and load at least one of stimulation programs 62 to therapy delivery circuitry 58. For example, in operation, processing circuitry 57 may access memory 60 to load one of therapy programs 63 to therapy delivery circuitry 52.

By way of example, processing circuitry 57 may access memory 60 to load one of therapy programs 63 to control therapy delivery circuitry 58 for delivering the electrical stimulation to patient 14. A clinician or patient 14 may select a particular one of therapy programs 63 from a list using a programming device, such as a patient programmer or a clinician programmer. Processing circuitry 57 may receive the selection via telemetry circuitry 61. Therapy delivery circuitry 58 delivers the electrical stimulation to patient 14 according to the selected program for an extended period of time, such as minutes or hours while patient 14 is asleep (e.g., as determined from the one or more sensors and/or sensing circuitry 56). For example, processing circuitry 57 may control switch circuitry 59 to couple electrodes 30 to therapy delivery circuitry 58.

Therapy delivery circuitry 58 delivers electrical stimulation according to stimulation parameters. In some examples, therapy delivery circuitry 58 delivers electrical stimulation in the form of electrical pulses. In such examples, relevant stimulation parameters may include a voltage or current pulse amplitude, a pulse rate, a pulse width, a duty cycle, and/or the combination of electrodes 30 therapy delivery circuitry 58 uses to deliver the stimulation signal. In some examples, therapy delivery circuitry 58 delivers electrical stimulation in the form of continuous waveforms. In such examples, relevant stimulation parameters may include a voltage or current amplitude, a frequency, a shape of the stimulation signal, a duty cycle of the stimulation signal, or the combination of electrodes 30 therapy delivery circuitry 58 uses to deliver the stimulation signal.

In some examples, the stimulation parameters for the therapy programs 63 may be selected to cause protrusor muscles 42 and/or 46 to a protruded state (e.g., to open-up airway 48). An example range of stimulation parameters for the electrical stimulation that are likely to be effective in treating OSA (e.g., upon application to the hypoglossal nerves to cause protrusor muscles 42, 46 to protrude or upon application to motor points such as motor points 54A, 54B, 55A, and 55B), are as follows:

a. Frequency or pulse rate: between about 30 Hz and about 50 Hz. In some examples, the minimum target frequency is used which may achieve muscle tetany (e.g., constant contraction) and provide the required force to open the airway.

b. Current Amplitude: between about 0.5 milliamps (mA) and about 10 mA, and more generally from 0.5 mA to 3 mA, and approximately 1.5 mA.

c. Pulse Width: between about 100 microseconds (µs) and about 500 µs. In some examples, a pulse width of 150 us might be used for reduced power consumption. In some particular examples, the pulse width is approximately 210 µs. In some cases, shorter pulse widths may be used in conjunction with higher current or voltage amplitudes.

Processing circuitry 50 may select therapy programs 63 for alternating delivery of electrical stimulation between stimulating left protrusor muscles 42 and/or 46 and right protrusor muscles 42 and/or 46 on a time basis, such as in examples where two leads 20 are implanted. In some examples, there may be some overlap in the delivery of electrical stimulation so for some of amount of time both left and right protrusor muscles 42 and/or 46 are being stimulated. In some examples, there may be a pause in alternating stimulation (e.g., stimulate left protrusor muscles, a time period with no stimulation, then stimulate right protrusor muscles, and so forth). Processing circuitry 50 may also select therapy programs 63 selecting between different combinations of electrodes 30 for stimulating, such as to stimulate different locations of the hypoglossal nerve(s), which may help with fatigue as well as provide more granular control of how much to protrude tongue 40.

In the example of FIG. 4, therapy delivery circuitry 58 drives electrodes 30 of lead 20. Specifically, therapy delivery circuitry 58 delivers electrical stimulation (e.g., regulated current or voltage pulses at pulse rates and pulse widths described above) to tissue of patient 14 via selected electrodes 30A-30D carried by lead 20. A proximal end of lead 20 extends from housing 15 of IMD 16 and a distal end of lead 20 extends to a target therapy site, such as one or both hypoglossal nerves and/or motor points 54A, 55A, 54B, and/or 55B. Therapy delivery circuitry 58 may deliver electrical stimulation with electrodes on more than one lead and each of the leads may carry one or more electrodes, such as when patient 14 is implanted with two leads 20 in tongue 40 for stimulating both hypoglossal nerves simultaneously or bilaterally (e.g., one after the other) or both motor points 54A and 54B and/or motor points 55A and 55B. The leads may be configured as an axial lead with ring electrodes or segmented electrodes and/or paddle leads with electrode pads arranged in a two-dimensional array. The electrodes may operate in a bipolar or multi-polar configuration with other electrodes or may operate in a unipolar configuration referenced to an electrode carried by the device housing or "can" of IMD 16.

In some examples, processing circuitry 57 may control therapy delivery circuitry 58 to deliver or terminate the electrical stimulation based on patient input received via telemetry circuitry 61. Telemetry circuitry 61 includes any suitable hardware, firmware, software or any combination thereof for communicating with another device, such as an external programmer. Under the control of processing circuitry 57, telemetry circuitry 61 may receive downlink telemetry (e.g., patient input) from and send uplink telemetry (e.g., an alert) to a programmer with the aid of an antenna, which may be internal and/or external. Processing circuitry 57 may provide the data to be uplinked to the programmer and the control signals for telemetry circuitry 61 and receive data from telemetry circuitry 61.

Generally, processing circuitry 57 controls telemetry circuitry 61 to exchange information with a medical device programmer and/or another device external to IMD 16. Processing circuitry 57 may transmit operational information and receive stimulation programs or stimulation parameter adjustments via telemetry circuitry 61. Also, in some examples, IMD 16 may communicate with other implanted devices, such as stimulators, control devices, or sensors, via telemetry circuitry 61.

Power source 62 delivers operating power to the components of IMD 16. Power source 62 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever electrical stimulation is to occur.

Figure 5:
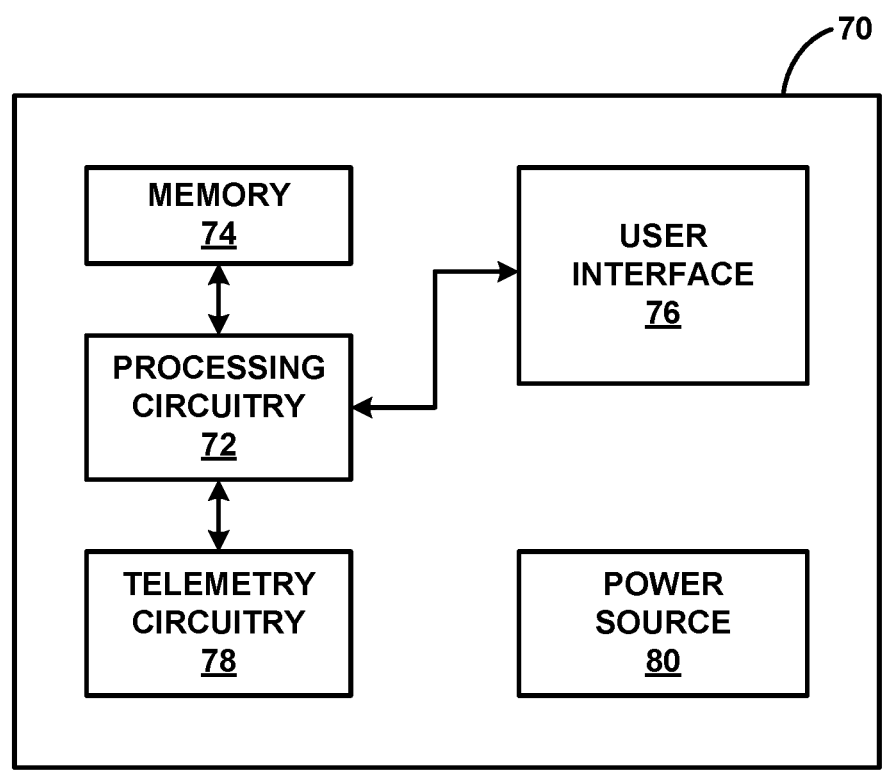
FIG. 5 is a block diagram illustrating an example configuration of an external programmer.

FIG. 5 is a block diagram illustrating an example configuration of an external programmer 70. While programmer 70 may generally be described as a hand-held computing device, the programmer may be a notebook computer, a cell phone, or a workstation, for example. As illustrated in FIG. 5, external programmer 70 may include processing circuitry 72, memory 74, user interface 76, telemetry circuitry 78, and power source 80.

In general, programmer 70 comprises any suitable arrangement of hardware, alone or in combination with software and/or firmware, to perform the techniques attributed to programmer 70, and processing circuitry 72, user interface 76, and telemetry module 78 of programmer 70. Examples of processing circuitry 72 may include one or more processors, such as one or more microprocessors, DSPs, ASICs, FPGAs, or any other equivalent integrated or discrete logic circuitry, as well as any combinations of such components. Examples of memory 74 include RAM, ROM, PROM, EPROM, EEPROM, flash memory, a hard disk, a CD-ROM, comprising executable instructions for causing the one or more processors to perform the actions attributed to them. Moreover, although processing circuitry 72 and telemetry circuitry 78 are described as separate circuitry, in some examples, processing circuitry 72 and telemetry circuitry 78 are functionally integrated. In some examples, processing circuitry 72 and telemetry circuitry 78 correspond to individual hardware units, such as ASICs, DSPs, FPGAs, or other hardware units.

In some examples, memory 74 may further include program information (e.g., stimulation programs) defining the electrical stimulation, similar to those stored in memory 60 of IMD 16. The stimulation programs stored in memory 74 may be downloaded into memory 60 of IMD 16.

User interface 76 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processing circuitry 72 may present and receive information relating to electrical stimulation and resulting therapeutic effects via user interface 76. For example, processing circuitry 72 may receive patient input via user interface 76. The input may be, for example, in the form of pressing a button on a keypad or selecting an icon from a touch screen.

Processing circuitry 72 may also present information to the patient in the form of alerts related to delivery of the electrical stimulation to patient 14 or a caregiver via user interface 76. Although not shown, programmer 70 may additionally or alternatively include a data or network interface to another computing device, to facilitate communication with the other device, and presentation of information relating to the electrical stimulation and therapeutic effects after termination of the electrical stimulation via the other device.

Telemetry circuitry 78 supports wireless communication between IMD 16 and programmer 70 under the control of processing circuitry 72. Telemetry circuitry 78 may also be configured to communicate with another computing device via wireless communication techniques, or direct communication through a wired connection. In some examples, telemetry circuitry 78 may be substantially similar to telemetry circuitry 61 of IMD 16 described above, providing wireless communication via an RF or proximal inductive medium. In some examples, telemetry circuitry 61 may include an antenna, which may take on a variety of forms, such as an internal or external antenna.

Examples of local wireless communication techniques which may be employed to facilitate communication between programmer 70 and another computing device include RF communication according to the 802.11 or Bluetooth specification sets, infrared communication (e.g., according to the IrDA standard), or other standard or proprietary telemetry protocols. In this manner, other external devices may be capable of communicating with programmer 70 without needing to establish a secure wireless connection.

Power source 80 delivers operating power to the components of programmer 70. Power source 80 may include a battery and a power generation circuit to produce the operating power. In some examples, the battery may be rechargeable to allow extended operation.

It should be noted system 10, and the techniques described herein, may not be limited to treatment or monitoring of a human patient. In alternative examples, system 10 may be implemented in non-human patients, e.g., primates, canines, equines, pigs, and felines. These other animals may undergo clinical or research therapies benefiting from the subject matter of this disclosure. Various examples are described herein, such as the following examples.

Figure 6:
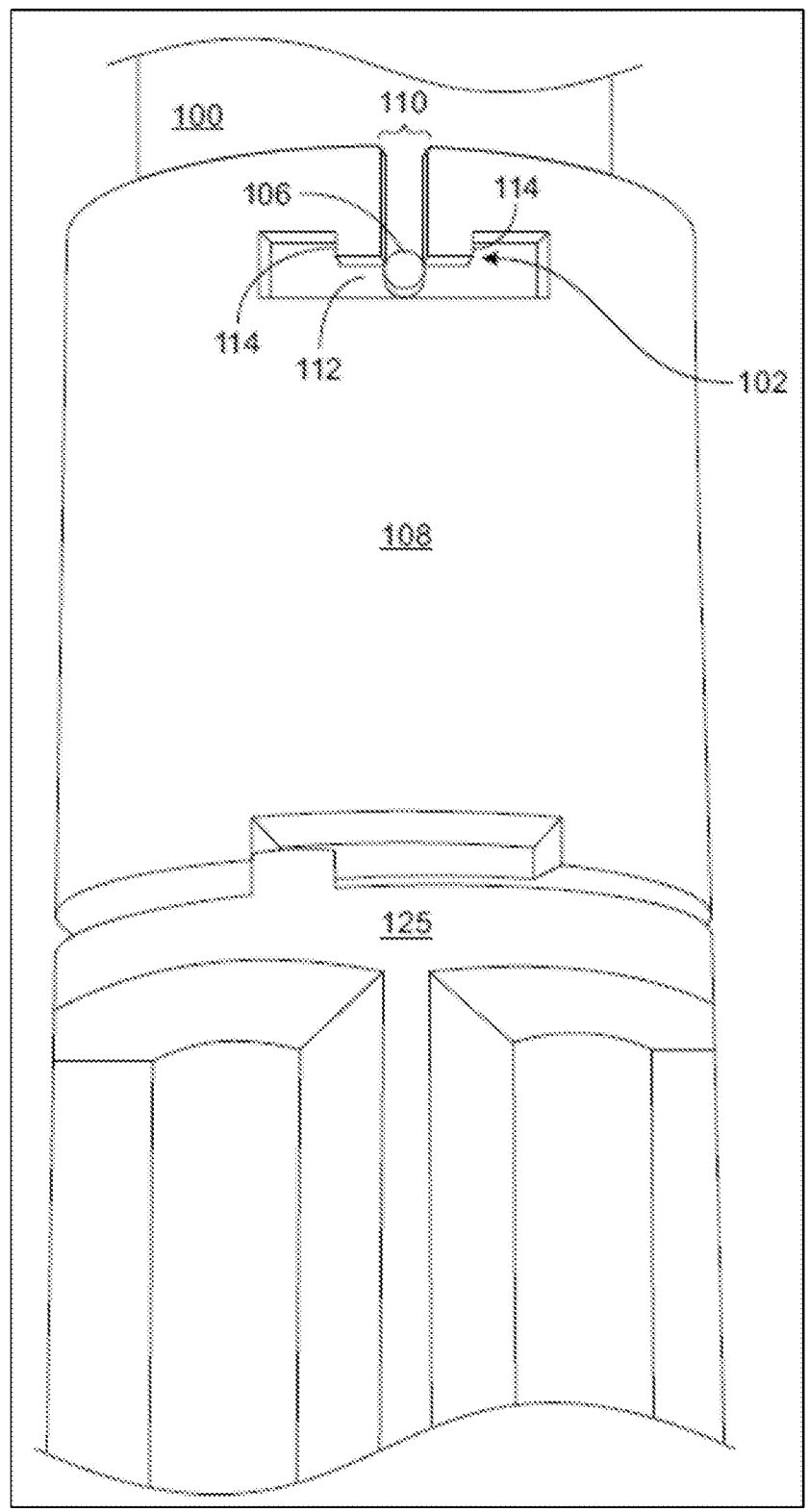
FIG. 6 is a pictorial illustration of a sheath for a combination trialing and chronic OSA lead according to one or more examples of this disclosure.

FIG. 6 is a pictorial illustration of a sheath 100 for a combination trialing and chronic OSA lead 20 according to one or more examples. In an example, sheath 100 may cover lead body 20 in whole or in part. For example, sheath 100 may extend to cover all of lead body 20 including electrodes 30 without preventing patient tissue stimulation during the trialing period. In another example, sheath 100 covers fixation member(s) 32 to prevent patient tissue fixation until after the trialing period of implantation is complete. A twist and lock notch mechanism 102 may be incorporated into trialing adaptor 125 at proximal end 24. In another example, trialing adapter 125, twist and lock notch mechanism 102 and sheath 100 are one integrated piece.

After the trialing period is completed, the trialing adapter 125, twist and lock notch mechanism 102 and sheath 100 are all removed to release fixation member(s) 32 and turn implantable lead 20 from a trialing lead to a chronic lead. Twist and lock notch mechanism 102 may line up with a connector pin 106 on the trialing adaptor 125 and be locked in place to secure the sheath 100 to lead body 20 and prevent deploying of the fixation member(s) 32. Once the decision to permanently implant the lead body 20 is made, the physician may disconnect proximal end 24 of lead 20 from a trialing stimulator (not shown). Twist and lock notch mechanism 102 is slightly rotated and trialing adapter 125 may then be explanted. Then the physician may pull back sheath 100 over lead body 20 and exposing fixation member(s) 32 to deploy. Proximal end 24 of lead 20 may then be coupled to connector assembly 17 of IMD 16 (i.e., as shown in FIG. 1) and lead 20 may be chronically deployed.

In another example, sheath 100 may be locked into place prior to deployment of OSA lead 20. Sheath 100 may be slid over lead 20. Receiving opening 110 may receive connector pin 106 into twist and lock notch mechanism 102 as sheath 100 is slid over lead 20. Once within chamber 112, locking head 108 may be turned to the right or left to lock connector pin 106 fully within chamber 112. Locking head 108 may be pulled back slightly to secure connector pin 106 within notches 114 on either side on chamber 112. This may assist locking head 108 from being inadvertently slid over connector pin during implantation or during the trialing process when the OSA lead 20 may need to be moved multiple times.

Figure 7:
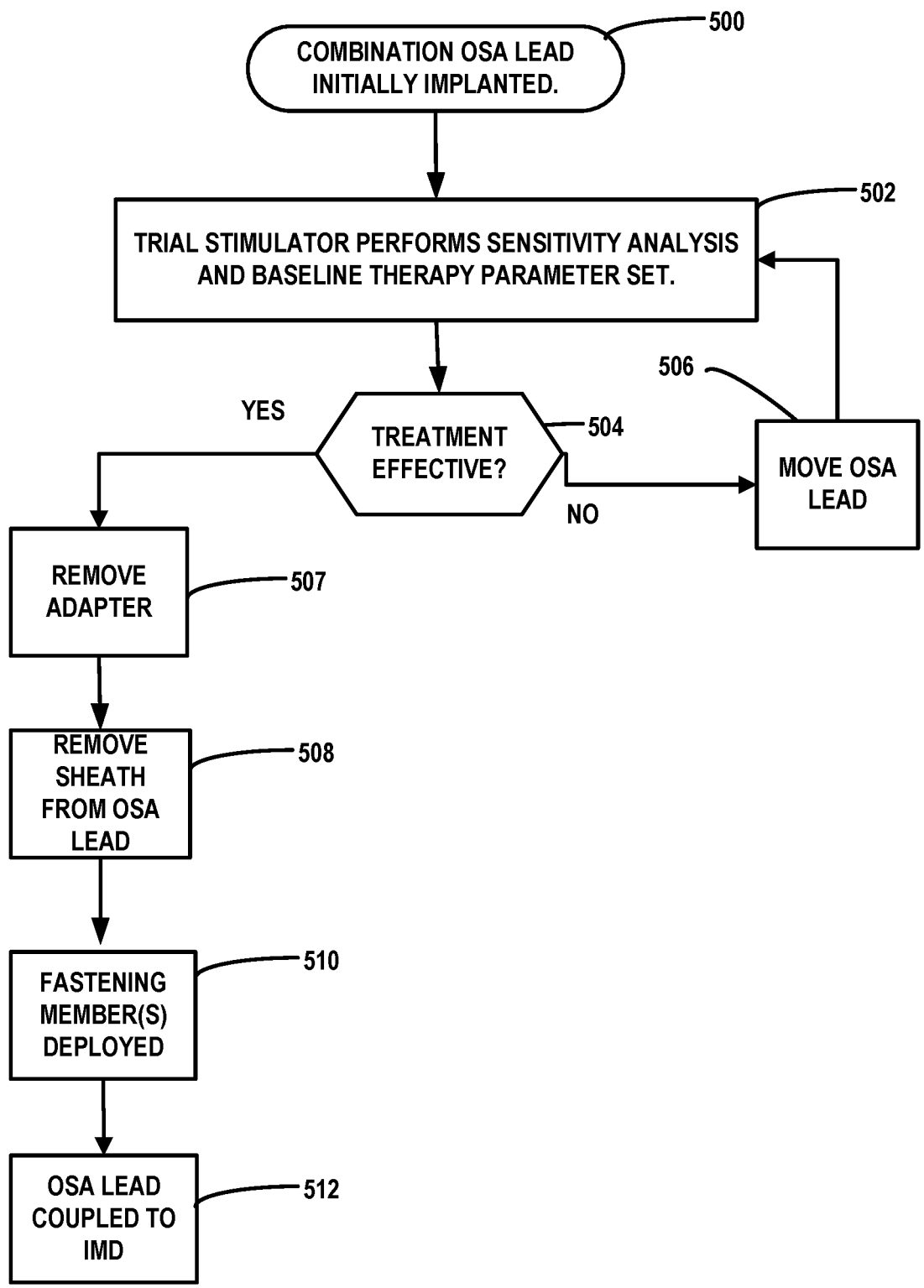
FIG. 7 is a flow diagram for a process of implantation of a combination trialing and chronic OSA lead according to one or more examples of this disclosure.

FIG. 7 is a flow diagram for a process of implantation of a combination trialing and chronic OSA lead according to one or more examples. In a first example, combination OSA lead 20 is implanted by an implanting physician (500). During the trialing phase, OSA lead 20 may be coupled to an external medical device configured to provide stimulation (e.g., a trailing stimulator). However, an implantable medical device may be used instead. For purposes of example, an external medical device, also called trial stimulator, is described as the medical device used for trialing.

The trial stimulator performs the sensitivity analysis and determination of a baseline therapy parameter set (502). The implanting physician may evaluate, over the trialing period, the effectiveness of the OSA treatment (504). If the implant location of OSA lead 20 is not proving effective in treatment of the patient's OSA, the implanting physician may choose to move OSA lead 20 to another location within protrusor muscles 42A, 42B, and 46 of tongue 40 and begin the trial stimulation period over again (506). If treatment is proving effective, the implanting physician may choose to end the trialing period. The trialing adaptor 125 is disconnected from the trialing stimulator coupling the trail stimulator to OSA lead 20(507). Locking head 108 is rotated to align receiving opening 110 with connector pin 106. Trialing adaptor 125 and sheath 100 may be explanted from OSA lead 20 (508). Fixation member(s) 32 become exposed to the patient's tissue upon removal of sheath 100 and fixation member(s) 32 secure OSA lead 20 in place (510). OSA lead 20 may be coupled to IMD 16 which is implanted for chronic OSA treatment (512). In another example, sheath 100 does not need to be removed, but instead is only pulled toward proximal end 24 until fixation member(s) 32 are exposed and OSA lead 20 is fixated in place. Sheath 100 does not necessarily need to explanted from the patient's body, but instead may be left in place as long as sheath 100 no longer covers fixation member(s) 32 and OSA lead 20 is held in place for chronic OSA therapy.

Separate surgeries are no longer required to remove the trialing lead and implant a chronic lead, and thus the infection risk is reduced. Additionally, sheath 100 prevents deployment of the fixation member(s) 32 during the trial period to provide ease of movement of OSA lead 20 during the trialing period, if it is necessary to reposition or remove the lead 20.

The example described above provides for an OSA lead 20 which is a trialing lead and a chronic lead, and therefore, a combination lead. The example above provides for a lead 20 which is used in the trailing process and when the trialing process is complete the lead 20 is in a chronic placement. The trialing lead may be made a chronic lead and implanted for long-term use. Example techniques, discussed below, include a sheath 100 for an implantable lead 20 which prevents tines 31 (FIG. 1) on the implantable lead 20 from deploying during the trialing procedure. Sheath 100 may then be removed, and the tines 31 are deployed to anchor the implantable lead 20 for chronic use.

Figure 8A:
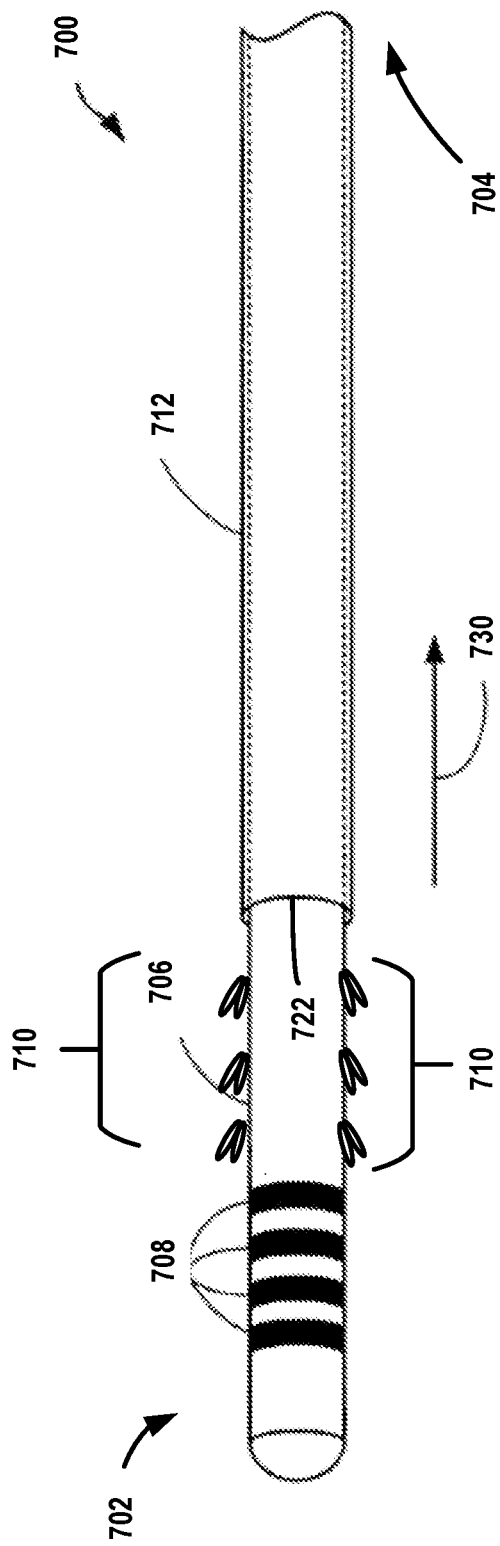
FIG. 8A is a perspective drawing of a sheath covering a lead prior to implantation and removed after the lead is correctly positioned in a patient after a trialing period.

FIG. 8A is a perspective drawing of a sheath 712 covering a lead 700 prior to implantation and removed after lead 700 is correctly positioned in a patient after a trialing period. In another example, lead 700 may have a proximal end 704 and a distal end 702 which define an elongated lead body 706. One or more electrodes 708 are disposed on the lead body 706 at the distal end 702. Fixation member(s) 710 (e.g., tines as shown) are disposed on elongated lead body 706 of lead 700. Fixation member(s) 710 are configured to secure lead 700 to tissue within patient 14. Fixation member(s) 710 are disposed on lead 700 at a proximal location to the one or more electrodes 708 of lead 700. A sheath 712 is configured to enclose at least a portion of lead 700 and cover fixation member(s) 710.

FIG. 8A shows lead 700 with sheath 712 being removed from lead body 706 in a direction indicated by arrow 730. Once lead 700 is positioned so electrodes 708, are adjacent to a target tissue site, which has been determined through trialing, the clinician may begin removing sheath 712 as shown. As sheath 712 is removed, one or more fixation member(s) 710 may be exposed to the adjacent tissue to fix lead body 706 in position. The fixation member(s) 710 may include balloon elements, fixation structures, adhesives, or other in situ formed or activated fixation elements discussed herein. In FIG. 7A, fixation member(s) 710 are shown as tines. In other embodiments, the clinician may remove sheath 712 in sections as fixation elements need to be deployed or as necessary to ensure proper fixation within the patient.

As previously discussed, a lead in accordance with the disclosure may be fixed at a target stimulation site with one or more fixation member(s) deployed after the lead is implanted in a patient (i.e., in situ) and a trialing period has determined the patient may be treated with an implantable lead and a suitable stimulation site has been found.

Figure 8B:
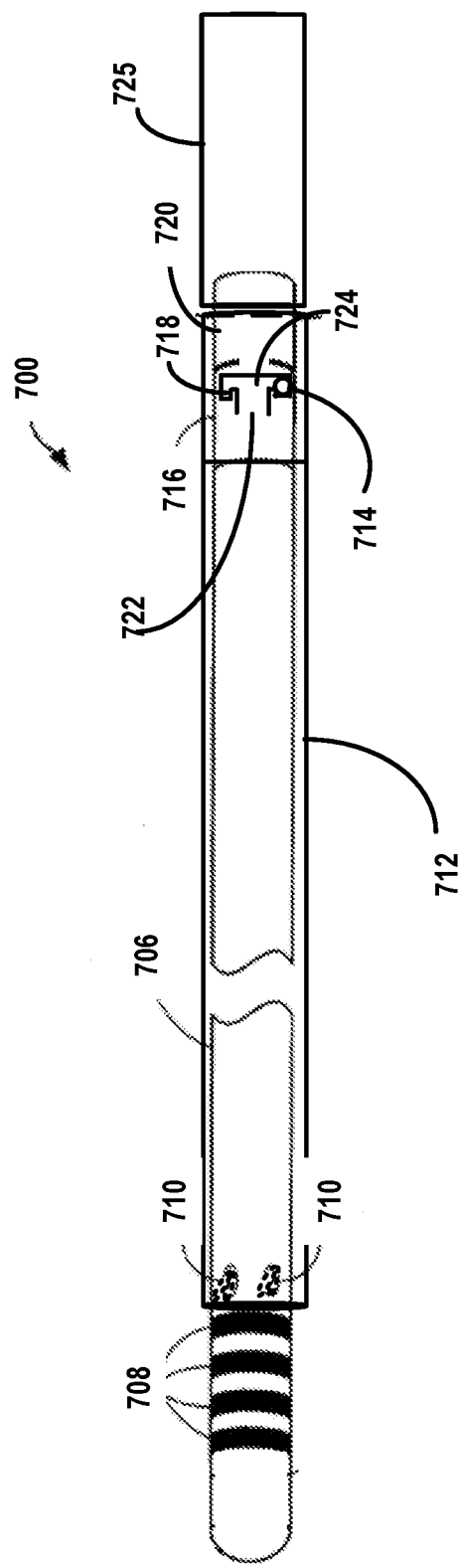
FIG. 8B is a perspective drawing of a sheath covering a combination trialing and chronic lead in accordance with one or more examples of this disclosure.

FIG. 8B is a perspective drawing of a sheath 712 covering a combination trialing and chronic lead 700 in accordance with one or more examples. In an example, connector pin 714 is located on sheath 712 and may be received by a twist and lock notch mechanism 716 located on a locking head 720. The twist and lock notch mechanism 716 has a receiving opening 722 configured to receive the connector pin 714. A chamber 724 within the twist and lock notch mechanism 716 may receive the connector pin 714. Notches 718 within the chamber 724 may be configured to secure the connector pin 714 within the twist and lock notch mechanism 716.

After implantation of OSA lead 700, patient 14 going through a trialing period which may be a couple of hours, a couple of days up to a couple of weeks. Regardless of the trialing period, sheath 712 remains in place, covering fixation members 710 during the trialing phase. Sheath 712 remains in place as proximal end 704 of sheath 712 is coupled to lock and notch mechanism 716. Specifically, connector pin 714, which has been received by receiving opening 722 is within notch 718 to prevent movement of sheath 712 in any direction.

After the trialing period is completed, trailing adapter 725 is disconnected from the trailing stimulator. Trailing stimulator 725 may then be disconnected from lead 700. This disconnection may be in most any fashion such as set screws which connect the conductors of lead 700 to the conductors of trialing adaptor 725. After removal of the trailing adapter 725, the clinician may simply pull on lock and notch mechanism 716 to pull the lock and notch mechanism 716 and sheath 712 from lead body 706. The proximal end of lead 700 may then be coupled to the connector 17 of IMD 16. The IMD 16 may then be implanted within a pocket of patient 14 as discussed above.

FIGS. 9A-9B are perspective drawings illustrating leads with fixation member(s) activated by a sheath removal. Lead 204 is an embodiment of lead 20 of FIGS. 1-2. The distal portion of lead 204 is shown in FIG. 9A, which includes lead body 208 (partially shown in phantom lines), electrodes 210, and fixation member(s) 212 and 214. The distal end of sheath 206 is also shown. Sheath 206 may be used to cover electrodes 210 and fixation member(s) 212 and 214 until lead 204 has finished the trialing phase and been implanted at the target tissue site within patient 14. Sheath 206 may separate fixation member(s) 212 and 214 from surrounding tissue until the trailing phase is complete and lead 204 is properly placed at the target tissue site. Once lead 204 is correctly positioned by the clinician, the clinician removes sheath 206 from lead body 208 to expose electrodes 210 and fixation member(s) 212 and 214 to the surrounding tissue. In FIG. 9A, sheath 206 is shown to be partially removed to expose fixation member(s) 214 at the distal end of lead 204.

Lead 204 may also include fixation member(s) similar to fixation member(s) 212 and 214 on the opposite side of lead body 208 (not shown). Each fixation member(s) 212 and 214 is disposed on longitudinal outer surface 208A of lead body 208 and includes tines. Each fixation member(s) 212 and 214 may each protrude (in a radial direction) slightly from longitudinal outer surface 208A of lead body 208, when sheath 206 is removed from covering each of the fixation member(s) 212 and 214. Alternatively, fixation member(s) 212 and 214 may be disposed in a recess of the lead body 208 so each fixation member(s) is flush with longitudinal outer surface 208A of lead body 208 and may be embedded in longitudinal outer surface 208A lead body 208 when sheath 206 covers fixation member(s) 212 and 214.

FIG. 9B shows lead 216, which includes elongated lead body 220 (partially shown in phantom lines), electrodes 222, and fixation member(s) 224, 226, 228, 230 and 232. Fixation member(s) 224 are disposed proximal to electrodes 222 while fixation member(s) 232 are disposed distal to the electrodes 222, which is a similar arrangement as fixation member(s) 212 and 214 of lead 204. Fixation member(s) 226, 228 and 230 are disposed between each electrode 222. Fixation member(s) 226, 228 and 230 bond lead 216 to the target tissue close to electrodes 222, thereby minimizing the distance between electrodes 222 and the target tissue during the duration of stimulation therapy. Alternatively, any number of fixation member(s) may be disposed on any longitudinal outer surface of elongated lead body 220. In addition, fixation member(s) may not need to be of uniform shapes and sizes to customize lead 216 for implantation at any tissue site.

Sheath 218 is configured to receive elongated lead body 220 and sized to cover fixation member(s) 224, 226, 228, 230, and 232 until lead 216 is thorough the trialing process and correctly placed within patient 14. In the view shown in FIG. 9B, sheath 218 has been partially withdrawn to expose fixation member(s) 228, 230 and 232. Various examples are described herein, such as the following examples.

Example 1: A system comprising a lead having a proximal end and a distal end and defining an elongated lead body, one or more electrodes disposed on the lead, a fixation member disposed on the elongated lead body of the lead, wherein the fixation member is configured to secure the lead to tissue within a patient, and wherein the fixation member is disposed on the lead such that the fixation member is closer to the proximal end than the one or more electrodes of the lead, a trialing adaptor configured to receive the proximal end of the lead and is removable when a trialing period is completed, and a sheath configured to enclose at least a portion of the lead and cover the fixation member, wherein the sheath is configured to remain in place over the at least a portion of the lead during the trialing period.

Example 2: The system of example 1, further comprising a connector pin disposed on the sheath.

Example 3: The system of example 2, further comprising a twist and lock notch mechanism located at the distal end of the elongated lead body, wherein the twist and lock notch mechanism has a receiving opening configured to receive the connector pin.

Example 4: The system of example 3, further comprising a chamber within the twist and lock notch mechanism which receives the connector pin.

Example 5: The system of example 4, further comprising notches within the chamber configured to secure the connector pin within the twist and lock notch mechanism.

Example 6: The system of any of examples 1-5, wherein the fixation member is at least one pair of collapsible tines.

Example 7: The system of example 6, wherein the pair of collapsible tines expand upon removal of the sheath from cover of the pair of collapsible tines.

Example 8: The system of example 7, wherein the pair of expanding tines contact the patient tissue and secure the lead within the patient tissue.

Example 9: The system of any of examples 1-8, wherein the trialing adaptor is configured to couple the lead to a trial stimulator during the trialing period and includes a proximal end that provides a percutaneous connection to the trial stimulator.

Example 10: The system of any of examples 1-9, wherein the lead comprises proximal connectors at the proximal end for coupling into an implantable medical device (IMD) for therapy delivery after the trialing period.

Example 11: A system comprising an implantable medical lead configured to couple to a medical device to deliver a therapy from the medical device to a target therapy delivery site in a patient, one or more electrodes disposed on the lead, a fixation member disposed on the lead and configured to secure the lead to tissue of the patient at a plurality of points distributed around the lead, wherein the fixation member is at a location distal to the medical device to deliver therapy, and a sheath configured to receive the lead and cover the fixation member, wherein the sheath is configured to remain in place over the at least a portion of the lead during a trialing period.

Example 12: The system of example 11, further comprising a connector pin located proximal to the one or more electrodes extending outward radially from the implantable medical lead.

Example 13: The system of example 12, further comprising a twist and lock mechanism configured to receive the connector pin within a chamber of the twist and lock mechanism.

Example 14: The system of example 13, further comprising a receiving channel on the twist and lock mechanism configured to receive the connector pin within the twist and lock mechanism.

Example 15: The system of any of examples 11-14, wherein the sheath is configured to be removed after a trialing period to deploy the fixation member to secure the implantable medical lead to a patient's tissue.

Example 16: A system comprising a medical lead comprising, an elongated lead body having a proximal end and a distal end, one or more electrodes disposed on the lead body distal end, a fixation member disposed on the elongated lead body of the lead, wherein the fixation member is configured to secure the lead to tissue within a patient, and wherein the fixation member is disposed proximal to the one or more electrodes, a sheath configured to cover the fixation member for a duration of a trialing period, wherein the sheath is configured to be removed from the lead to activate the fixation member and secure the medical lead to a tissue within the patient after the trialing period is completed, and an electrical stimulator configured to deliver electrical stimulation therapy to a tongue of the patient via the one or more electrodes of the medical lead to cause the tongue to protrude for treating obstructive sleep apnea (OSA).

Example 17: The system of example 16, wherein the one or more electrodes comprise a plurality of electrodes and a plurality of fixation members are arranged longitudinally along the lead in alternating relationship with the plurality of electrodes.

Example 18: The system of any of examples 16 and 17, wherein the fixation member is configured to secure the lead to tissue within a patient at opposite sides of the elongated lead body.

Example 19: The system of any of examples 16-18, wherein the fixation member is a pair of collapsible tines where the pair of collapsible tines are prevented from securing the lead to tissue within the patient while the sheath remains covering the pair of collapsible tines.

Example 20: The system of any of examples 16-19, further comprising a trialing adaptor configured to retain the sheath and remove the sheath upon completion of the trialing period.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete logic circuitry, or other processing circuitry, as well as any combinations of such components, remote servers, remote client devices, or other devices. The term "processor" or "processing circuitry" may refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. For example, any module described herein may include electrical circuitry configured to perform the features attributed to that particular module, such as fixed function processing circuitry, programmable processing circuitry, or combinations thereof.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that may, over time, change (e.g., in RAM or cache).

Various examples have been described herein. Any combination of the described operations or functions is contemplated. These and other examples are within the scope of the following claims.

What is claimed is:

1. A system comprising:
   a lead having a proximal end and a distal end and defining an elongated lead body, wherein the lead is configured to be used for a trialing period when the lead is coupled to an external trial stimulator that is not to be implanted within a patient, and the same lead is configured to be used for chronic therapy when the lead is coupled to an implantable medical device after the trialing period;
   one or more electrodes disposed on the lead;
   a fixation member disposed on the elongated lead body of the lead, wherein the fixation member is configured to secure the lead to tissue within the patient;
   a trialing adaptor configured to receive the proximal end of the lead and configured to be removable from the lead when the trialing period is completed,
   wherein the trialing adaptor is configured to couple the lead to the external trial stimulator,
   wherein a first end of the trialing adaptor is configured to be within a body of the patient and a second end of the trialing adaptor is configured to exit from the body of the patient to provide a percutaneous connection from the lead to the external trial stimulator, and
   wherein the proximal end of the lead includes one or more proximal connectors configured to couple to the implantable medical device upon implantation of the implantable medical device within the body of the patient after the trialing period; and
   a sheath configured to enclose at least a portion of the lead and cover the fixation member, wherein the sheath is configured to remain in place over the at least a portion of the lead during the trialing period, wherein the sheath includes a connector pin disposed on the sheath that is configured to lock into the trialing adaptor, wherein the connector pin, when locked into the trialing adaptor, is configured to prevent movement of the sheath, and wherein the connector pin, when unlocked from the trialing adaptor, is configured to allow movement of the sheath.

2. The system of claim 1, wherein the trialing adaptor comprises a twist and lock notch mechanism located at the distal end of the elongated lead body, wherein the twist and lock notch mechanism has a receiving opening configured to receive the connector pin.

3. The system of claim 2, further comprising a chamber within the twist and lock notch mechanism which receives the connector pin.

4. The system of claim 3, further comprising notches within the chamber configured to secure the connector pin within the twist and lock notch mechanism.

5. The system of claim 1, wherein the fixation member is at least one pair of collapsible tines.

6. The system of claim 5, wherein the pair of collapsible tines expand upon removal of the sheath from cover of the pair of collapsible tines.

7. The system of claim 6, wherein the pair of expanding tines contact the patient tissue and secure the lead within the patient tissue.

* * * * *